United States Patent
Ahn et al.

(10) Patent No.: US 9,658,235 B2
(45) Date of Patent: May 23, 2017

(54) PI-EXTENDED ACEDAN DERIVATIVES, THEIR APPLICATION FOR TWO-PHOTON MICROSCOPY IMAGING, AND THEIR APPLICATION FOR TWO-PHOTON MICROSCOPY IMAGING OF AMYLOID-BETA PLAQUE IN AN ALZHEIMER'S DISEASE ANIMAL MODEL

(71) Applicant: POSTECH ACADEMY-INDUSTRY FOUNDATION, Pohang-si, Gyeongsangbuk-do (KR)

(72) Inventors: Kyo Han Ahn, Pohang-si (KR); Hyunsoo Moon, Uijeongbu-si (KR); Dokyoung Kim, Pohang-si (KR); Ki Hean Kim, Pohang-si (KR); Hye Gun Ryu, Daegu (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 22 days.

(21) Appl. No.: 14/745,973

(22) Filed: Jun. 22, 2015

(65) Prior Publication Data
US 2016/0202263 A1 Jul. 14, 2016

(30) Foreign Application Priority Data
Jan. 14, 2015 (KR) .......... 10-2015-0006973

(51) Int. Cl.
*G01N 33/58* (2006.01)
*G01N 21/64* (2006.01)
(Continued)

(52) U.S. Cl.
CPC ....... *G01N 33/582* (2013.01); *A61K 49/0021* (2013.01); *C07D 311/78* (2013.01);
(Continued)

(58) Field of Classification Search
None
See application file for complete search history.

(56) References Cited

FOREIGN PATENT DOCUMENTS

KR    10-2013-0130254 A    12/2013

OTHER PUBLICATIONS

Kim et al., "Two-Photon Absorbing Dyes with Minimal Autofluorescence in Tissue Imaging: Application to in Vivo Imaging of Amyloid-β Plaques with a Negligible Background Signal", J.Am.Chem. Soc., 2015, 137, 6781-6789.*
(Continued)

*Primary Examiner* — Jianfeng Song
(74) *Attorney, Agent, or Firm* — Vorys, Sater, Seymour & Pease LLP; Mih Suhn Koh

(57) ABSTRACT

Provided are acedan derivatives having an extended π bond, a method for preparing the acedan derivatives, and a method for two-photon microscopy imaging of amyloid-beta plaque using the acedan derivatives; more particularly, to two-photon absorbing fluorescent compounds having a longer absorption wavelength and emission wavelength than acedan and acedan derivatives which are conventional two-photon absorbing fluorophores. The compounds provided may be usefully used for in vivo imaging studies by imaging cells or tissue using the compounds, and may also be usefully used for diagnosing Alzheimer's disease by imaging amyloid-beta plaque using the compounds.

12 Claims, 19 Drawing Sheets
(9 of 19 Drawing Sheet(s) Filed in Color)

(51) Int. Cl.
*C07D 311/92* (2006.01)
*G01N 33/68* (2006.01)
*C07D 311/78* (2006.01)
*C07D 311/94* (2006.01)
*A61K 49/00* (2006.01)

(52) U.S. Cl.
CPC .......... *C07D 311/92* (2013.01); *C07D 311/94* (2013.01); *G01N 21/6428* (2013.01); *G01N 33/6896* (2013.01); *G01N 2021/6439* (2013.01); *G01N 2333/4709* (2013.01); *G01N 2800/2821* (2013.01)

(56) References Cited

OTHER PUBLICATIONS

Moon et al., "Development of π-Extended Acedan Derivatives and Their Application for Two-Photon Microscopy Imaging of Amyloid-β Plaque" in the 114th General Meeting of the Korean Chemical Society on Oct. 15, 2014.

Moon et al., "π-Extended acedan derivatives and their applications to bioimaging" in Workshop of Center for Electro-Photo Behaviors in Advanced Molecular Systems on Jan. 5, 2015.

Kim et al., "Recent development of two-photon fluorescent probes for bioimaging", Org. Biomol. Chem., Jul. 14, 2014, vol. 12, No. 26, pp. 4550-4566.

\* cited by examiner

PI-EXTENDED ACEDAN DERIVATIVES, THEIR APPLICATION FOR TWO-PHOTON MICROSCOPY IMAGING, AND THEIR APPLICATION FOR TWO-PHOTON MICROSCOPY IMAGING OF AMYLOID-BETA PLAQUE IN AN ALZHEIMER'S DISEASE ANIMAL MODEL

CROSS-REFERENCE TO RELATED APPLICATION

This application claims priority to and the benefit of Korean Patent Application No. 2015-0006973, filed on Jan. 14, 2015, the disclosure of which is incorporated herein by reference in its entirety.

BACKGROUND

1. Field of the Invention

The present invention relates to the acedan derivatives having an extended π bond, which are novel two-photon absorbing fluorescent compounds, a method of preparing the acedan derivatives, an application of the acedan derivatives for bioimaging and for two-photon microscopy imaging of amyloid-beta plaque in an animal model with Alzheimer's disease.

2. Discussion of Related Art

Bioimaging techniques based on a fluorescence signal are widely used as a method of visualizing not only an organelle but also tissue in an animal model. Among the techniques, the development of fluorescent probes expands the application area for specific material analysis and imaging in vivo.

Most fluorescent probes which have been reported up to now are based on one-photon absorption fluorophores, and undergo the imaging process in accordance with one-photon microscopy (OPM). However, the use of general one-photon microscopy has a disadvantage in tissue imaging in that the image quality is reduced due to strong light scattering and only shallow tissue at a depth of 100 μm or less may be imaged.

The use of a nonlinear optical microscope provides insensitivity to the above-described light scattering and properties suitable for high-resolution imaging. Two-photon microscopy (TPM) is one type of the nonlinear optical microscopy, which allows a fluorophore to be excited by simultaneous irradiation with two photons having energy with a wavelength corresponding to a half of the one photon which is used in one-photon microscopy (OPM). Furthermore, a two-photon fluorophore is only excited at a focal point, and thus an image with high resolution may be implemented. Accordingly, the use of two-photon microscopy has advantages for its application in bioimaging such as high tissue permeability, an increased photon-penetrating depth, low photo-damage to bio-tissue, low photo-bleaching, etc. Further, the interference effect from autofluorescent materials in vivo is small.

The number of two-photon absorbing (TPA) fluorophores having optimal characteristics required for bioimaging is limited. As a representative two-photon absorbing fluorophore, acedan (1-(6-dimethylaminonaphthalene-2-yl) ethanone) represented by the following Formula 10 is a dipolar dye having a D-π-A structure in which an electron donor (D) and an electron acceptor (A) are included in an aromatic ring (π-system), and has a high photostability and large two-photon absorption cross-section value, and thus is used in the two-photon microscopy imaging study for a living cell and tissue.

[Formula 10]

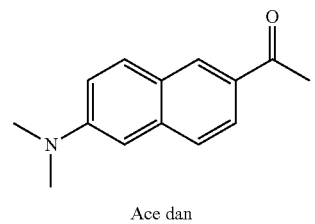

Ace dan

However, acedan has a shorter maximum absorption wavelength (<400 nm) and maximum emission wavelength (<550 nm), and thus has a disadvantage in that acedan is highly affected by the autofluorescence of fluorophores in vivo such as tryptophan, tyrosine, phenylalanine, retinol, riboflavin and nicotinamide adenine dinucleotide, etc.

In addition, the general acedan derivatives have a problem in that a low-power laser is used, or a process of removing an autofluorescent signal by signal processing is further needed so as to avoid the effect from autofluorescence and obtain a clear two-photon fluorescence microscope image. Accordingly, in order to avoid the effect from autofluorescence and obtain a clear two-photon fluorescence microscope image, novel two-photon absorbing fluorophores which are capable of being excited at a longer wavelength of about 900 nm such that the fluorophores are suitable for biological optical windows should be ensured.

As another example of the acedan derivative, GCTPOC represented by the following Formula 2 is a dipolar dye having a D-π-A structure, which is based on a green fluorescent protein chromophore (GFP chromophore, p-HOBDI) represented by the following Formula 3. However, the above-described fluorophore also shows a maximum absorption band in a short wavelength area (<400 nm) like acedan, and thus has a problem in that the autofluorescence due to a fluorophore in vivo is shown at the two-photon excitation condition (<800 nm).

[Formula 2]

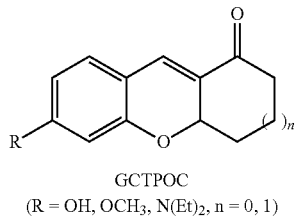

GCTPOC
(R = OH, OCH$_3$, N(Et)$_2$, n = 0, 1)

[Formula 3]

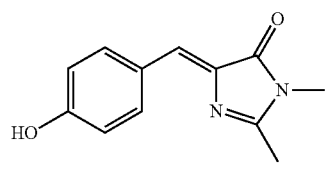

GFP chromophore (p-HOBDI)

SUMMARY OF THE INVENTION

In order to overcome the problem of the conventional technique, the inventors of the present invention developed novel two-photon absorbing fluorophores allowing two-photon excitation at a long wavelength of about 900 nm, thereby completing the present invention.

Accordingly, the objective of the present invention is directed to providing a novel two-photon absorbing fluorophores. More specifically, the present invention is directed to providing a method of imaging cells and tissue and a method of imaging amyloid-beta plaque (Aβ plaque) in an individual with Alzheimer's disease (AD) using the compound. Further, the present invention is directed to providing a method of preparing the compound.

However, the technical objective to be achieved by the present invention is not limited to the above-described subjects, and other objectives which are not mentioned above will be clear to those skilled in the art from the following description.

In order to achieve the above-described objective of the present invention, the present invention provides acedan derivatives represented by the following Formula 1:

[Formula 1]

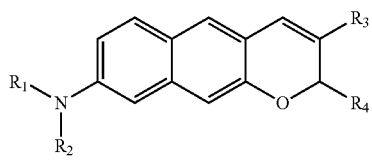

In Formula 1, $R_1$ and $R_2$ each may be a hydrogen (H), a methyl (Me) group, an allyl group, an unsubstituted alkyl group having 2 to 12 carbon atoms, or a cyclic secondary amine; $R_3$ may

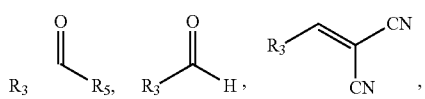

or a cycloalkyl group connected with $R_4$ through a ring; $R_5$ may be a methyl (Me), an ethyl, or and an unsubstituted alkyl group having 2 to 12 carbon atoms; $R_4$ may be a hydrogen or a cycloalkyl group connected with $R_3$ through a ring; and the cycloalkyl groups connected with each other through a ring may be

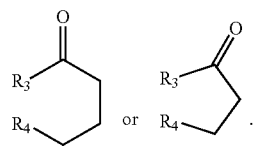

According to an embodiment of the present invention, the acedan derivatives may be compounds selected from the group consisting of compounds of the following Formulas 4 to 8:

[Formula 4]

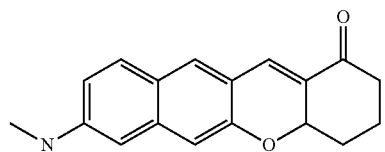

[Formula 5]

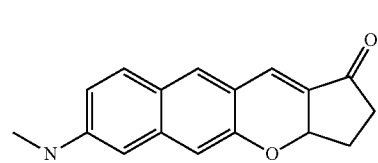

[Formula 6]

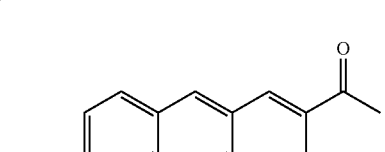

[Formula 7]

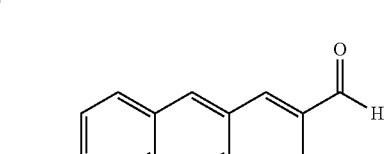

[Formula 8]

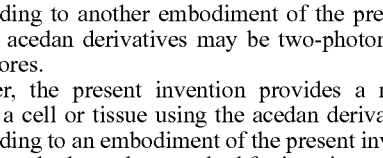

According to another embodiment of the present invention, the acedan derivatives may be two-photon absorbing fluorophores.

Further, the present invention provides a method for imaging a cell or tissue using the acedan derivatives.

According to an embodiment of the present invention, the imaging method may be a method for imaging amyloid-beta plaque in a cell or tissue.

According to another embodiment of the present invention, the imaging method may include treating a cell or tissue with the acedan derivatives and observing the cell or tissue using a fluorescent microscope.

According to still another embodiment of the present invention, the fluorescent microscope may be a one-photon fluorescence microscope or two-photon fluorescence microscope.

Further, the present invention provides a method for diagnosing Alzheimer's disease, which includes the acedan derivatives.

Further, the present invention provides a method for diagnosing Alzheimer's disease, which includes treating an individual with the acedan derivatives.

According to an embodiment of the present invention, the diagnostic method may include treating a cell or tissue with the acedan derivatives and observing the cell or tissue using a fluorescent microscope.

In addition, the present invention provides a method for preparing an acedan derivative represented by the following Formula 4 from 6-(dimethylamino)-3-hydroxy-2-naphthaldehyde, which includes synthesizing 8-(dimethylamino)-2,3,4a-tetrahydro-1H-benzo[b]xanthene-1-one by adding 2-cyclohexene-1-one and 1,4-diazabicyclo[2.2.2]octane to 6-(dimethylamino)-3-hydroxy-2-naphthaldehyde.

[Formula 4]

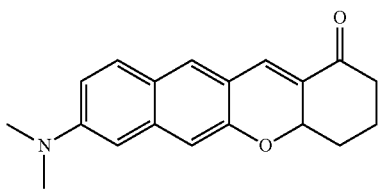

4

Further, the present invention provides a method for preparing an acedan derivative represented by the following Formula 5 from 6-(dimethylamino)-3-hydroxy-2-naphthaldehyde, which includes synthesizing 7-(dimethylamino)-3,3a-dihydrobenzo[g]cyclopenta[b]chromene-1(2H)-one by adding 2-cyclopentene-1-one and 1,4-diazabicyclo[2.2.2]octane to 6-(dimethylamino)-3-hydroxy-2-naphthaldehyde.

[Formula 5]

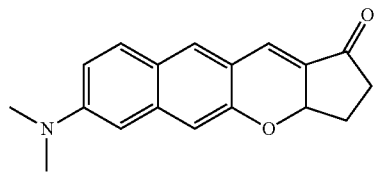

5

Further, the present invention provides a method for preparing an acedan derivative represented by the following Formula 6 from 6-(dimethylamino)-3-hydroxy-2-naphthaldehyde, which includes synthesizing 1-(8-(dimethylamino)-2H-benzo[g]chromene-3-yl)ethanone by adding 3-butene-2-one, magnesium iodide, tetramethylethylenediamine and 4-dimethylaminopyridine to 6-(dimethylamino)-3-hydroxy-2-naphthaldehyde.

[Formula 6]

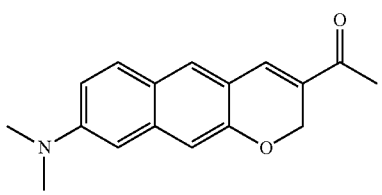

6

Further, the present invention provides a method for preparing an acedan derivative represented by the following Formula 7 from 6-(dimethylamino)-3-hydroxy-2-naphthaldehyde, which includes synthesizing 6-(dimethylamino)-3-(propynyl-2-oxy)-2-naphthaldehyde by adding propargyl bromide and potassium carbonate to 6-(dimethylamino)-3-hydroxy-2-naphthaldehyde, and then adding malononitrile and copper iodide thereto.

[Formula 7]

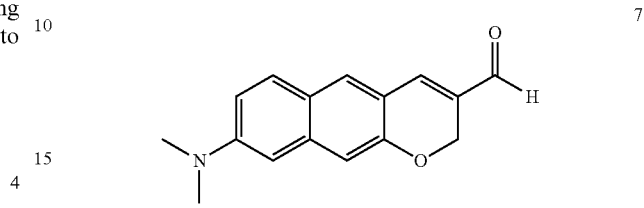

7

Further, the present invention provides a method for preparing an acedan derivative represented by the following Formula 8 from 6-(dimethylamino)-3-(propynyl-2-oxy)-2-naphthaldehyde, which includes synthesizing 2-(((8-dimethylamino)-2H-benzo[g]chromene-3-yl)methylene)malononitrile by adding malononitrile, copper iodide, and triethylamine to 6-(dimethylamino)-3-(propynyl-2-oxy)-2-naphthaldehyde.

[Formula 8]

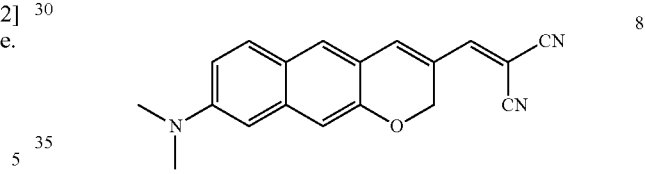

8

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
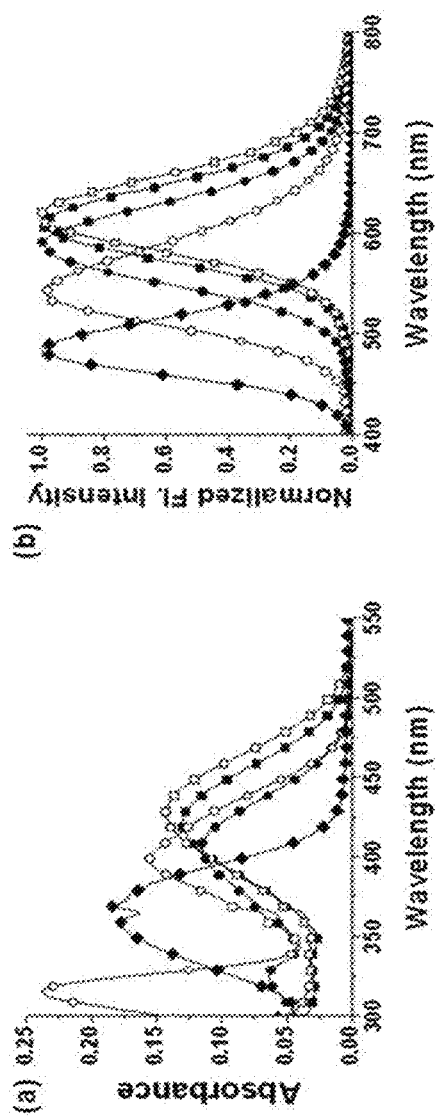
FIG. 1 illustrates absorption spectra (A) and normalized fluorescence emission spectra (B) of acedan (♦), compound 4a ($R_1$=$R_2$=Me) (■), compound 5a ($R_1$=$R_2$=Me) (□), compound 6a ($R_1$=$R_2$=Me) (●), and compound 7a ($R_1$=$R_2$=Me) (○) having a concentration of 10 μM in an ethanol (EtOH) solution.
Figure 2:
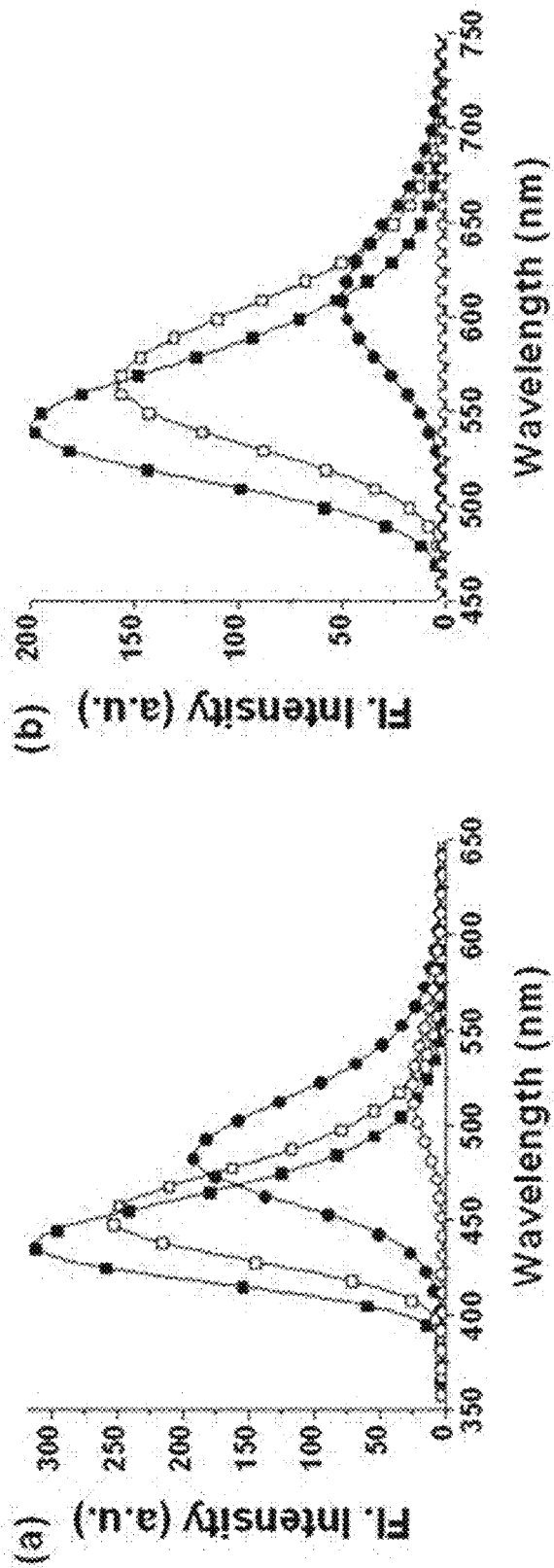
FIG. 2 illustrates fluorescence emission spectra of acedan (A) and compound 4a ($R_1$=$R_2$=Me) (B) having a concentration of 1 μM in a dichloromethane ($CH_2Cl_2$) (■), acetonitrile ($CH_3CN$) (□), ethanol (EtOH) (●), and a phosphate buffer saline (PBS) buffer solution (○) (10 mM, pH 7.4, 0.1%-dimethyl sulfoxide (DMSO) included)

The present invention is directed to providing acedan derivatives represented by the following Formula 1, which are novel two-photon absorbing fluorophores.

[Formula 1]

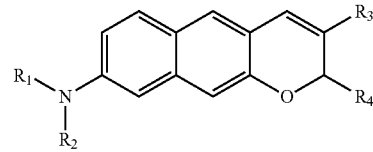

In Formula 1, $R_1$ and $R_2$ each may be a hydrogen (H), a methyl (Me) group, an allyl group, an unsubstituted alkyl group having 2 to 12 carbon atoms, or a cyclic secondary amine; $R_3$ may be from

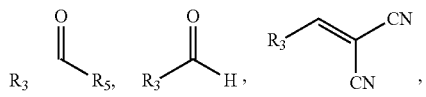

a functional group which may be easily derived from

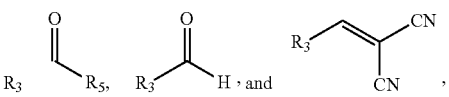

or a cycloalkyl group connected with $R_4$ through a ring; $R_5$ may be a methyl (Me), an ethyl, or and unsubstituted alkyl group having 2 to 12 carbon atoms; $R_4$ may be a hydrogen or a cycloalkyl group connected with $R_3$ through a ring; and the cycloalkyl groups connected with each other through a ring may be

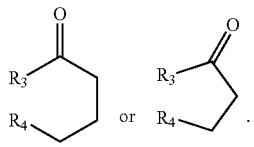

Preferably, the acedan derivatives may be compounds selected from the group consisting of compounds of the following Formulas 4a to 8a. In Formulas 4a to 8a, $R_1$ and $R_2$ each may be a hydrogen (H), a methyl (Me) group, an allyl group, an unsubstituted alkyl group having 2 to 12 carbon atoms, or a cyclic secondary amine

[Formula 4a]

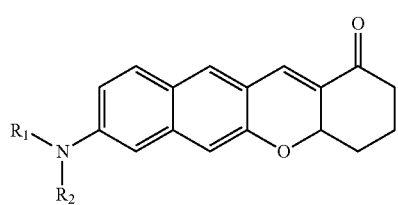

[Formula 5a]

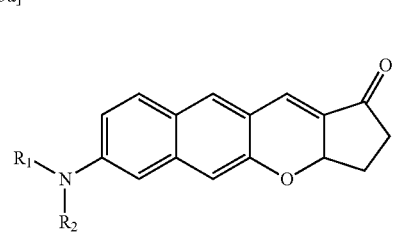

[Formula 6a]

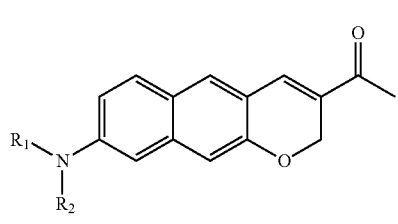

[Formula 7a]

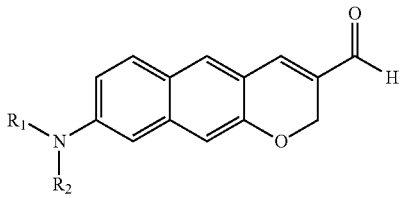

[Formula 8a]

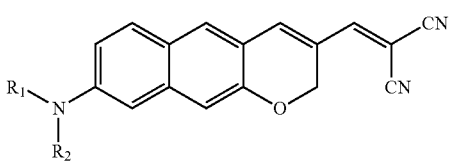

More preferably, the acedan derivatives may be compounds of the following Formulas 4 to 8, in which $R_1$ and $R_2$ are substituted with a methyl group.

[Formula 4]

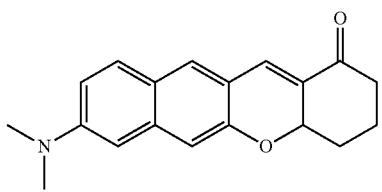

[Formula 5]

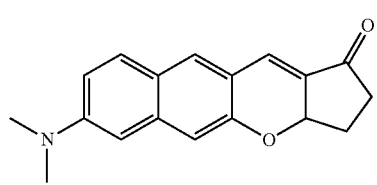

[Formula 6]

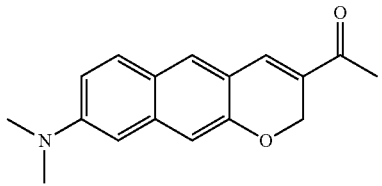

[Formula 7]

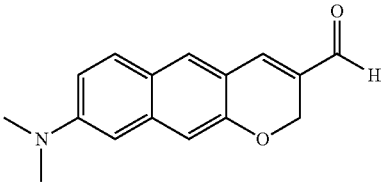

[Formula 8]

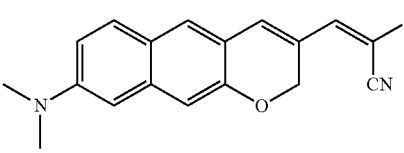

In an embodiment of the present invention, a cell or tissue of an animal model was treated with the acedan derivatives of the embodiment of the present invention, and as a result, it was determined that a more excellent fluorescence image than that of a conventional two-photon absorbing fluorophore could be provided (Examples 6 to 10).

Accordingly, the present invention may provide an imaging method for a cell or tissue and a diagnostic method for Alzheimer's disease using the acedan derivatives.

Hereinafter, preferred embodiments will be described to help in understanding of the present invention. However, the following embodiments are merely provided for ease of understanding the present invention, and content of the present invention is not limited to the following embodiments.

Example 1

Synthesis of compound 4a ($R_1$=$R_2$=Me) (8-dimethylamino)-2,3,4a)-tetrahydro-1H-benzo[b]xanthene-1-one)

A general synthesis process of compound 4a ($R_1$=$R_2$=Me) is shown in the following Reaction Formula 1.

[Reaction Formula 1]

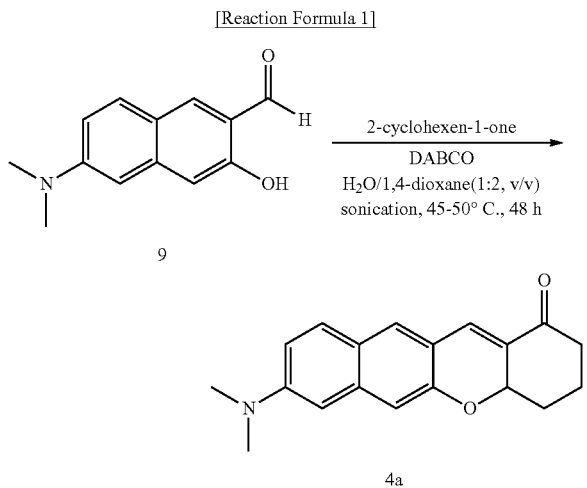

4a

The inventors of the present invention performed the synthesis of 8-(dimethylamino)-2,3,4a-tetrahydro-1H-benzo[b]xanthene-1-one which is the compound 4a ($R_1$=$R_2$=Me).

More specifically, $H_2O$/1,4-dioxane (3.0 mL, 1:2, v/v) was introduced into an airtight container including compound 9 which is a well-known synthesis-starting material (110 mg, 0.50 mmol), 2-cyclohexene-1-one (97 μL, 1.0 mmol), and 1,4-diazabicyclo[2.2.2]octane (28 mg, 0.25 mmol), and then the container was sealed. The mixture was stirred for 48 hours under ultrasonication at a temperature in the range of 45 to 50° C. After the temperature of the mixture was decreased to room temperature (25° C.) and a solvent was removed under the condition of a reduced pressure of 40 mbar, the mixture was refined (eluent: 10%-EtOAc/hexane) using a column chromatography method in which the mixture was passed through a silica gel (Merck-silica gel 60, 230-400 mesh) to obtain an orange solid compound 4a ($R_1$=$R_2$=Me) (56 mg, 38%; 40% of the compound 9 was recovered).

$^1$H NMR (CDCl$_3$, 300 MHz, 297 K, δ): 7.61-7.54 (m, 3H), 6.99-6.95 (m, 2H), 6.69 (d, J=2.1 Hz, 1H), 5.04-4.97 (m, 1H), 3.07 (s, 6H), 2.64-2.35 (m, 3H), 2.14-1.95 (m, 2H), 1.81-1.66 (m, 1H); $^{13}$C NMR (CDCl$_3$, 75 MHz, 298 K, δ): 197.36, 153.22, 149.88, 137.86, 132.14, 130.69, 130.30, 129.59, 122.74, 119.19, 114.35, 109.11, 104.80, 74.84, 40.47 (2 carbons), 38.82, 29.86, 18.12; HRMS: m/z calcd for $C_{19}H_{19}NO_2$, 293.3597. found, 293.1417.

Example 2

Synthesis of compound 5a ($R_1$=$R_2$=Me) (7-dimethylamino)-3,3a-dihydrobenzo[g]cyclopenta[b]chromene-1(2H)-one)

A general synthesis process of compound 5a ($R_1$=$R_2$=Me) is shown in the following Reaction Formula 2.

[Reaction Formula 2]

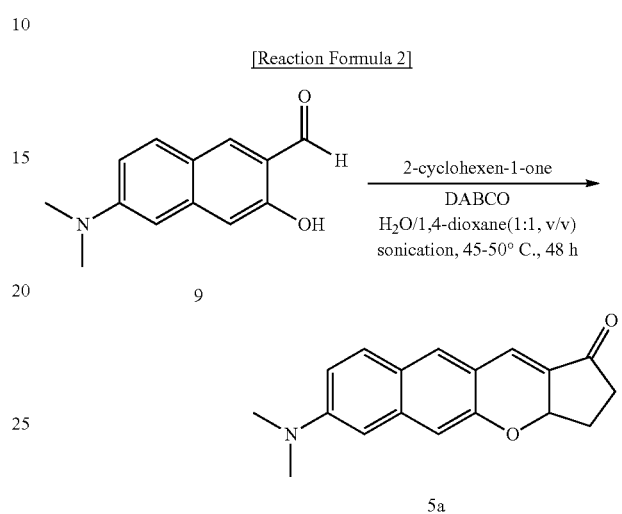

5a

The inventors of the present invention performed the synthesis of 7-(dimethylamino)-3,3a-dihydrobenzo[g]cyclopenta[b]chromene-1(2H)-one which is compound 5a ($R_1$=$R_2$=Me).

More specifically, $H_2O$/1,4-dioxane (1.8 mL, 1:1, v/v) was introduced into an airtight container including compound 9 which is a well-known synthesis-starting material (20 mg, 0.093 mmol), 2-cyclopentene-1-one (48 μL, 0.56 mmol), and 1,4-diazabicyclo[2.2.2]octane (11 mg, 0.095 mmol), and then the container was sealed. The mixture was stirred for 48 hours under ultrasonication at a temperature in the range of 45 to 50° C. After the temperature of the mixture was decreased to room temperature (25° C.) and a solvent was removed under the condition of a reduced pressure of 40 mbar, the mixture was refined (eluent: 5%-EtOAc/hexane) using a column chromatography method in which the mixture was passed through a silica gel (Merck-silica gel 60, 230-400 mesh) to obtain a yellow solid compound 5a ($R_1$=$R_2$=Me) (5.7 mg, 22%; 70% of the compound 9 was recovered).

$^1$H NMR (CDCl$_3$, 300 MHz, 296 K, δ): 7.60 (d, J=9.0 Hz, 1H), 7.57 (s, 1H), 7.37 (d, J=2.1 Hz, 1H), 7.02 (s, 1H), 6.98 (dd, J=9.02. 4 Hz, 1H), 6.69 (d, J=2.4 Hz, 1H), 5.31-5.25 (m, 1H), 3.08 (s, 6H), 2.76-2.56 (m, 2H), 2.44-2.31 (m, 1H), 2.22-2.11 (m, 1H); $^{13}$C NMR (CDCl$_3$, 75 MHz, 297 K δ): 201.35, 152.77, 150.02, 138.02, 131.93, 131.20, 129.56, 128.45, 122.72, 118.81, 114.46, 109.76, 104.82, 76.05, 40.45 (2 carbons), 37.12, 28.17; HRMS: m/z calcd. for $C_{18}H_{17}NO_2$, 279.3331. found, 279.1260.

Example 3

Synthesis of compound 6a ($R_1$=$R_2$=Me) (1-(8-(dimethylamino)-2H-benzo[g]chromene-3-yl)ethanone)

A general synthesis process of compound 6a ($R_1$=$R_2$=Me) is shown in the following Reaction Formula 3.

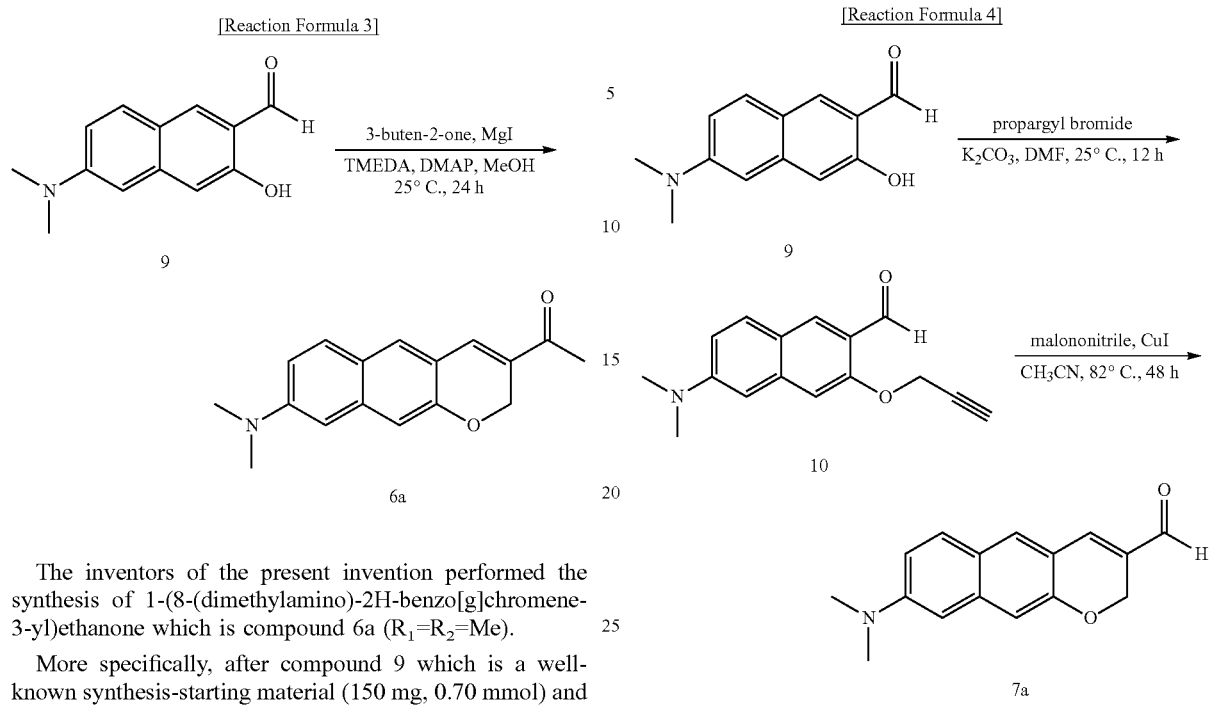

The inventors of the present invention performed the synthesis of 1-(8-(dimethylamino)-2H-benzo[g]chromene-3-yl)ethanone which is compound 6a ($R_1=R_2=Me$).

More specifically, after compound 9 which is a well-known synthesis-starting material (150 mg, 0.70 mmol) and 3-butene-2-one (170 μL, 2.1 mmol) were dissolved in methanol (MeOH, 1.0 mL) in a flask, the flask was filled with an argon gas at room temperature. Magnesium iodide (MgI) (20 mg, 0.0070 mmol) and tetramethylethylenediamine (TMEDA) (11 μL, 0.070 mmol) were dissolved in methanol (MeOH, 1.0 mL), and the methanol solution was introduced into the flask. 4-dimethylaminopyridine (DMAP) (8.6 mg, 0.070 mmol) was dissolved in methanol (MeOH, 0.50 mL), and the methanol solution was introduced into the flask. After the mixture was stirred at room temperature for 24 hours, an ammonium chloride ($NH_4Cl$) aqueous solution was introduced thereto. After the mixture was extracted using dichloromethane (2×20 mL), an organic layer was dried using anhydrous sodium sulfate. After a solvent was removed under the condition of a reduced pressure of 40 mbar, the dried extract was refined (eluent: 10%-EtOAc/hexane) using a column chromatography method in which the dried extract was passed through a silica gel (Merck-silica gel 60, 230-400 mesh) to obtain a yellow solid compound 6a ($R_1=R_2=Me$) (70 mg, 28%; 37% of the compound 9 was recovered).

$^1H$ NMR (CDCl3, 300 MHz, 297 K, δ): 7.59 (d, J=9.0 Hz, 1H), 7.48 (s, 1H), 7.44 (s, 1H), 6.98-6.94 (m, 2H), 6.69 (d, J=2.4 Hz, 1H), 5.02 (d, J=1.2 Hz, 2H), 3.07 (s, 6H), 2.42 (s, 3H); $^{13}C$ NMR ($CDCl_3$, 75 MHz, 298 K, δ): 195.86, 152.79, 149.87, 138.21, 134.60, 130.95, 129.51, 129.48, 122.50, 117.87, 114.26, 109.24, 104.79, 64.53, 40.47 (2 carbons), 24.96; HRMS: m/z calcd for $C_{17}H_{17}NO_2$, 267.3224. found, 267.1257.

Example 4

Synthesis of Compound 7a ($R_1=R_2=Me$)

A general synthesis process of compound 7a ($R_1=R_2=Me$) is shown in the following Reaction Formula 4.

<4-1> Synthesis of compound 10 (6-(dimethylamino)-3-(propynyl-2-oxy)-2-naphthaldehyde)

The inventors of the present invention performed the synthesis of 6-(dimethylamino)-3-(propynyl-2-oxy)-2-naphthaldehyde which is compound 10.

More specifically, after compound 9 which is a well-known synthesis-starting material (200 mg, 0.93 mmol) and potassium carbonate ($K_2CO_3$, 390 mg, 2.8 mmol) were dissolved in dimethylformamide (DMF, 6.5 mL) at room temperature, propargyl bromide (0.20 mL, 1.4 mmol) was added thereto. The mixture was stirred at room temperature for 12 hours, and then was extracted using ethyl acetate (2×10 mL). An organic layer was cleaned using water (10 mL) and saturated brine (10 mL), and was dried using anhydrous sodium sulfate. After a solvent was removed under the condition of a reduced pressure of 40 mbar, the next step was performed without a separate refining process.

<4-2> Synthesis of compound 7a ($R_1=R_2=Me$) (8-(dimethylamino)-2H-benzo[g]chromene-3-carbaldehyde)

The inventors of the present invention performed the synthesis of 8-(dimethylamino)-2H-benzo[g]chromene-3-carbaldehyde which is compound 7a ($R_1=R_2=Me$).

More specifically, after the compound 10 (37 mg, 0.15 mmol) which was obtained in Example 4-1 and copper iodide (CuI) were dissolved in acetonitrile ($CH_3CN$, 3.7 mL), the mixture was stirred for 48 hours at 82° C. using a silicon oil container. After the temperature of the mixture was decreased to room temperature and a solvent was removed under the condition of a reduced pressure of 40 mbar, the mixture was refined (eluent: 5%-EtOAc/hexane) using a column chromatography method in which the mixture was passed through a silica gel (Merck-silica gel 60, 230-400 mesh) to obtain an orange solid compound 7a ($R_1=R_2=Me$) (70 mg, 71%).

$^1$H NMR (CDCl$_3$, 300 MHz, 298 K, δ): 10.39 (s, 1H), 8.11 (s, 1H), 7.69 (d, J=9.3 Hz, 1H), 7.05-6.98 (m, 2H), 6.78 (d, J=2.1 Hz, 1H), 5.96-5.90 (m, 1H), 4.91 (dd, J=3.9, 1.8 Hz, 2H), 3.13 (s, 6H); $^{13}$C NMR (CDCl3, 75 MHz, 298 K, δ): 189.47, 153.62, 150.81, 135.13, 132.14, 130.22, 121.18, 121.11, 120.63, 119.32, 114.32, 113.84, 98.92, 65.18, 40.36 (2 carbons); HRMS: m/z calcd for C$_{16}$H$_{15}$NO$_2$, 253.2958. found, 253.1100.

Example 5

Synthesis of compound 8a (R$_1$=R$_2$=Me) (2-(((8-dimethylamino)-2H-benzo[g]chromene-3-yl)methylene)malononitrile)

A general synthesis process of compound 8a (R$_1$=R$_2$=Me) is shown in the following Reaction Formula 5.

[Reaction Formula 5]

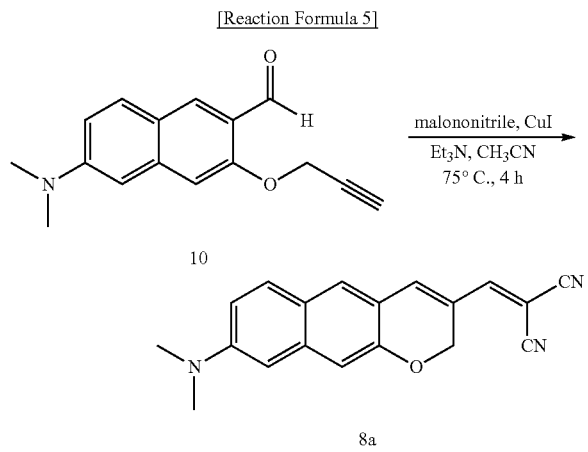

The inventors of the present invention performed the synthesis of 2-(((8-dimethylamino)-2H-benzo[g]chromene-3-yl)methylene)malononitrile which is the compound 8a (R$_1$=R$_2$=Me).

More specifically, after the compound 10 (220 mg, 0.93 mmol) which was obtained in Example 4-1, malononitrile (62 mg, 0.93 mmol), and copper iodide (CuI, 53 mg, 0.28 mmol) were dissolved in acetonitrile (CH$_3$CN, 6.0 mL), triethylamine (Et3N, 0.10 mL, 0.090 mmol) was added to the mixture. The mixture was stirred for 4 hours at 75° C. using a silicon oil container. After the temperature of the mixture was decreased to room temperature and a solvent was removed under the condition of a reduced pressure of 40 mbar, the mixture was refined (eluent: CH$_2$Cl$_2$) using a column chromatography method in which the mixture was passed through a silica gel (Merck-silica gel 60, 230-400 mesh) to obtain a red solid compound 8a (R$_1$=R$_2$=Me) (200 mg, 70%).

$^1$H NMR (CDCl3, 600 MHz, 293K, δ): 7.61 (d, J=9.0 Hz, 1H), 7.51 (s, 1H), 7.27 (s, 1H), 7.23 (s, 1H), 6.99 (dd, J=9.3, 2.7 Hz, 1H), 6.97 (s, 1H), 6.69 (d, J=2.4 Hz, 1H), 5.39 (s, 2H), 3.14 (s, 6H); $^{13}$C NMR (CDCl$_3$, 150 MHz, 293 K, δ): 155.49, 152.41, 150.66, 142.52, 139.46, 131.42, 130.37, 126.80, 122.67, 117.91, 114.88, 114.51, 113.72, 109.32, 104.52, 64.47, 40.31 (2 carbons). HRMS: m/z calcd for C$_{19}$H$_{15}$ON$_3$, 301.1215. found, 301.1215.

Example 6

Determination of Absorption Properties of Two-Photon Absorbing Fluorophore

The inventors of the present invention determined the absorption properties of the compounds 4a to 8a (R$_1$=R$_2$=Me) which are two-photon absorbing fluorophores according to the embodiment of the present invention, and the results are shown in FIGS. 1(A), 6, 9(A), 11 and 12.

More specifically, in order to determine the absorption properties of two-photon absorbing fluorophores, the inventors of the present invention filled quartz cells (114F-QS, Hellma Analytics) having a path length of 1 cm with an ethanol solution (1%-DMSO included) which included the compounds 4a to 7a (R$_1$=R$_2$=Me) having a concentration of 10 μM to measure absorption spectra. The results thereof with absorbance as a y-axis and light wavelength as an x-axis are shown in FIG. 1(A). Referring to FIG. 1(A), it may be determined that maximum absorption wavelengths (λ$_{abs}$ (nm)) of the compounds 4a to 7a (R$_1$=R$_2$=Me) were longer than that of conventional acedan (compound 1). Further, in order to determine the absorption properties of the compound 8a (R$_1$=R$_2$=Me) which is a two-photon absorbing fluorophore, quartz cells having a path length of 1 cm were filled with a toluene, dioxane, ethyl acetate, dichloromethane, ethanol, dimethylforamide, dimethyl sulfoxide (DMSO), and PBS buffer solution (1%-DMSO included) which included the compound 8a (R$_1$=R$_2$=Me) having a concentration of 10 μM to measure absorption spectra. The results thereof with absorbance as a y-axis and light wavelength as an x-axis are shown in FIG. 9(A). The absorption spectra were measured using an HP 8453 UV/Vis spectrophotometer.

Figure 11:
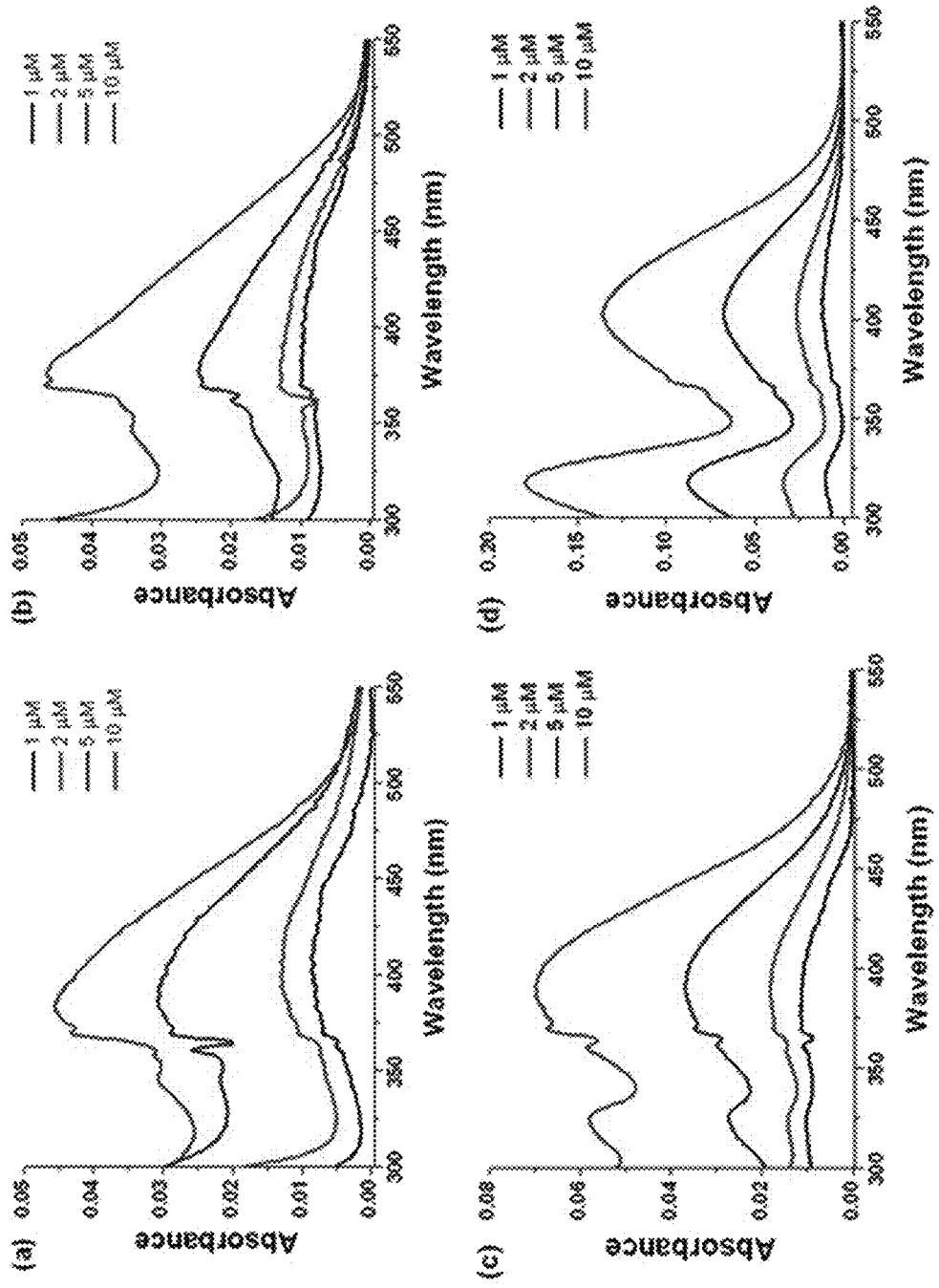
FIG. 11 illustrates absorption spectra (A, B, C and D, respectively) of compound 4a ($R_1=R_2=Me$), compound 5a ($R_1=R_2=Me$), compound 6a ($R_1=R_2=Me$), and compound 7a ($R_1=R_2=Me$) having a concentration of 1, 2, 5, and 10 μM, in a PBS buffer solution (10 mM, pH 7.4, DMSO of less than 1% included)

Quartz cells having a path length of 1 cm were filled with a PBS buffer solution (10 mM, pH 7.4, DMSO of less than 1% included) which included the compounds 4a to 7a (R$_1$=R$_2$=Me) each having concentrations of 1, 2, 5 and 10 μM to measure absorption spectra. The results thereof with absorbance as a y-axis and light wavelength as an x-axis are shown in FIGS. 11(A, B, C and D). Referring to FIG. 11, it may be determined that the compounds 4a to 7a (R$_1$=R$_2$=Me) each having concentrations of 1, 2 and 5 μM showed sufficient solubility in a PBS buffer solution.

Figure 12:
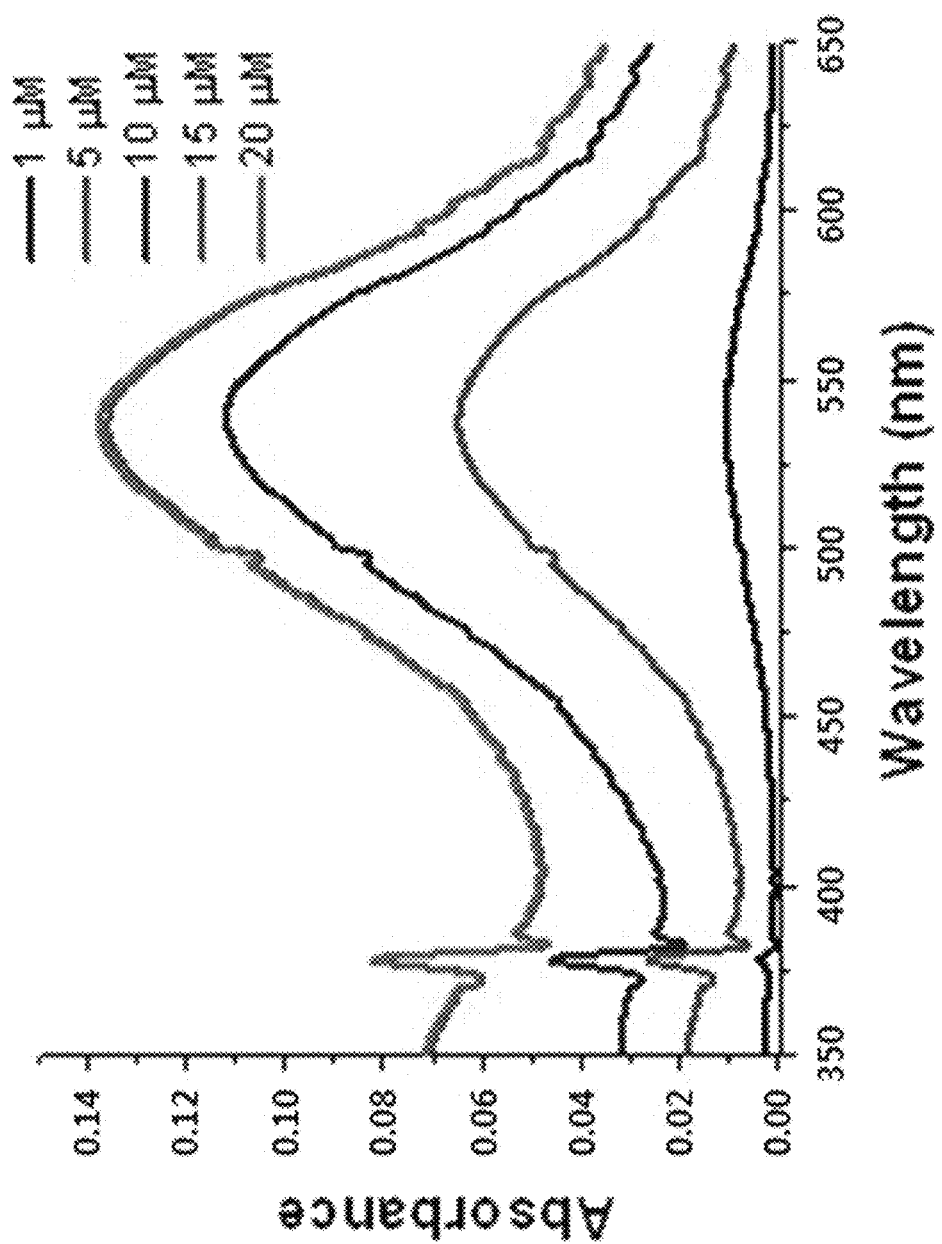
FIG. 12 illustrates absorption spectra of compound 8a ($R_1=R_2=Me$) having a concentration of 1, 5, 10, 15 and 20 μM in a PBS buffer solution (10 mM, pH 7.4, DMSO of less than 2% included)

Quartz cells having a path length of 1 cm were filled with a PBS buffer solution (10 mM, pH 7.4, DMSO of less than 1% included) which included the compound 8a (R$_1$=R$_2$=Me) each having concentrations of 1, 5, 10, 15 and 20 μM to measure absorption spectra. The results thereof with absorbance as a y-axis and light wavelength as an x-axis are shown in FIG. 12. Referring to FIG. 12, it may be determined that the compound 8a (R$_1$=R$_2$=Me) each having concentrations of 1, 5 and 10 μM showed sufficient solubility in a PBS buffer solution.

Figure 6:
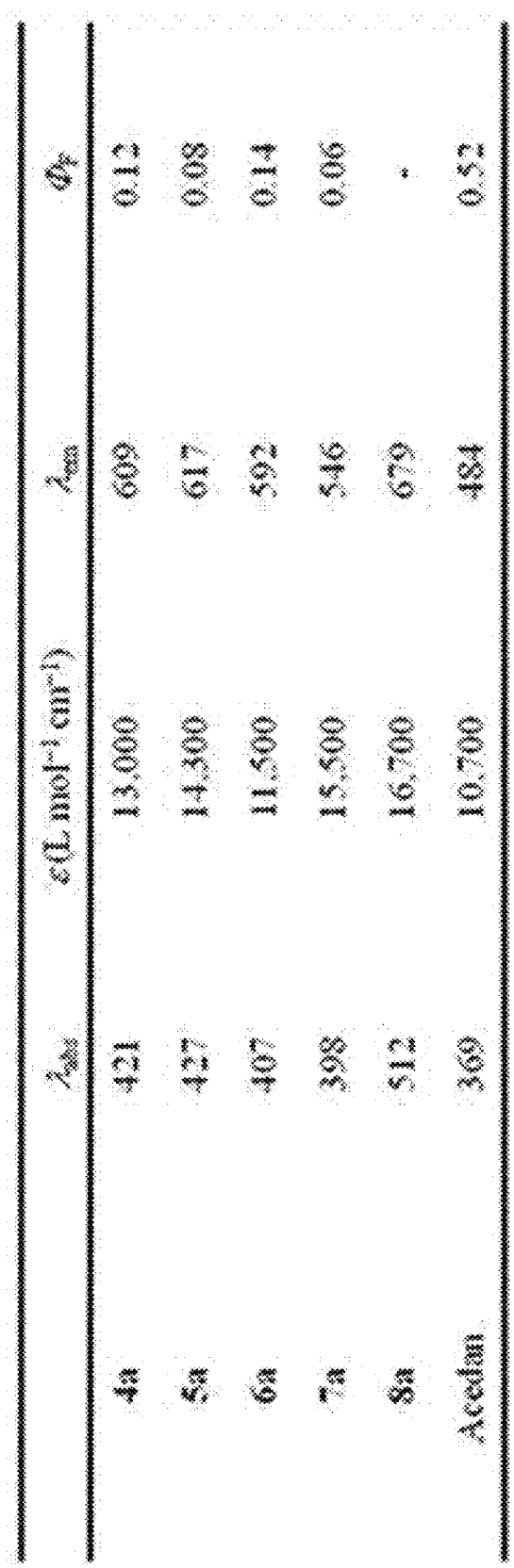
FIG. 6 illustrates a maximum absorption wavelength ($\lambda_{abs}$), a molar extinction coefficient (ε), a maximum emission wavelength ($\lambda_{em}$), and a fluorescence quantum yield ($\Phi_F$) of acedan and compounds 4a to 8a ($R_1=R_2=Me$) having a concentration of 10 μM in an ethanol solution.

Thereafter, a molar extinction coefficient (ε(Lmol$^{-1}$cm$^{-1}$)) in a maximum absorption wavelength was calculated with respect to an ethanol solution (1%-DMSO included) which included the compounds 4a to 8a (R$_1$=R$_2$=Me) having a concentration of 10 μM, and the result is shown in FIG. 6. Referring to FIG. 6, it may be determined that the molar extinction coefficients (ε>11,500) for the two-photon absorbing fluorophores (particularly, compounds 4a to 8a (R$_1$=R$_2$=Me)) according to the embodiment of the present invention were larger than that (ε=10,700) of acedan known as a conventional two-photon absorbing fluorophore.

Example 7

Determination of Fluorescent Properties of Two-Photon Absorbing Fluorophore The inventors of the present invention determined the fluorescent properties of the compounds 4a to 8a ($R_1$=$R_2$=Me) which are two-photon absorbing fluorophores according to the embodiment of the present invention, and the results were shown in FIGS. 1(B), 2, 4, 6 To 8, 9(A) and 13 to 15.

Figure 7:
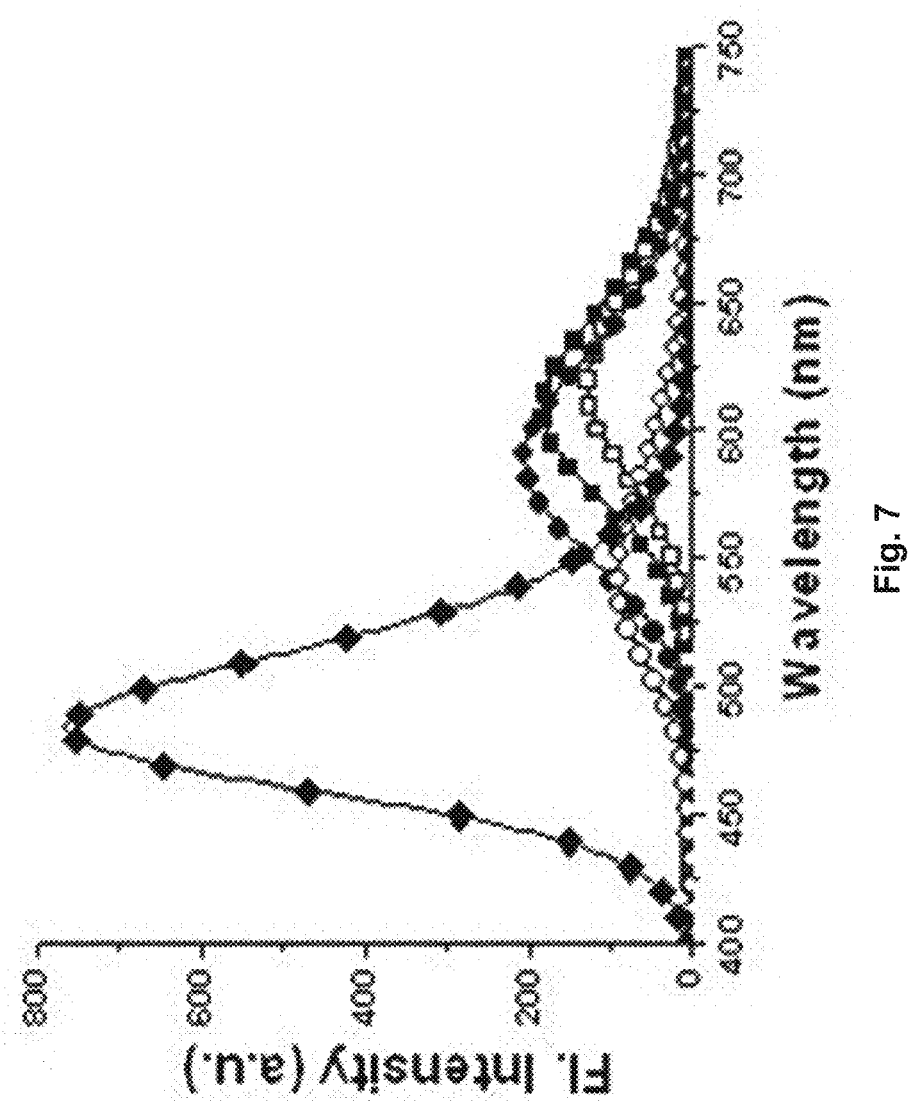
FIG. 7 illustrates fluorescence emission spectra of acedan (♦), compound 4a ($R_1=R_2=Me$) (■), compound 5a ($R_1=R_2=Me$) (□), compound 6a ($R_1=R_2=Me$) (●), and compound 7a ($R_1=R_2=Me$) (○) having a concentration of 10 μM in an ethanol (EtOH) solution.

More specifically, in order to determine the fluorescent properties of two-photon absorbing fluorophores, the inventors of the present invention filled quartz cells having a path length of 1 cm with an ethanol solution (1%-DMSO included) which included the compounds 4a to 7a ($R_1$=$R_2$=Me) having a concentration of 10 μM to measure fluorescence spectra (fluorescence spectra were measured using a photon technical international fluorescence system). The results thereof with normalized fluorescence as a y-axis and light wavelength as an x-axis are shown in FIG. 1(B) and with fluorescence intensity as a y-axis and light wavelength as an x-axis are shown in FIG. 7. Referring to FIG. 7, it may be determined that maximum emission wavelengths ($\lambda_{em}$ (nm)) of the compounds 4a to 7a ($R_1$=$R_2$=Me) which are two-photon absorbing fluorophores according to the embodiment of the present invention were longer than that of conventional acedan (compound 1) known as a conventional two-photon absorbing fluorophore.

Figure 13:
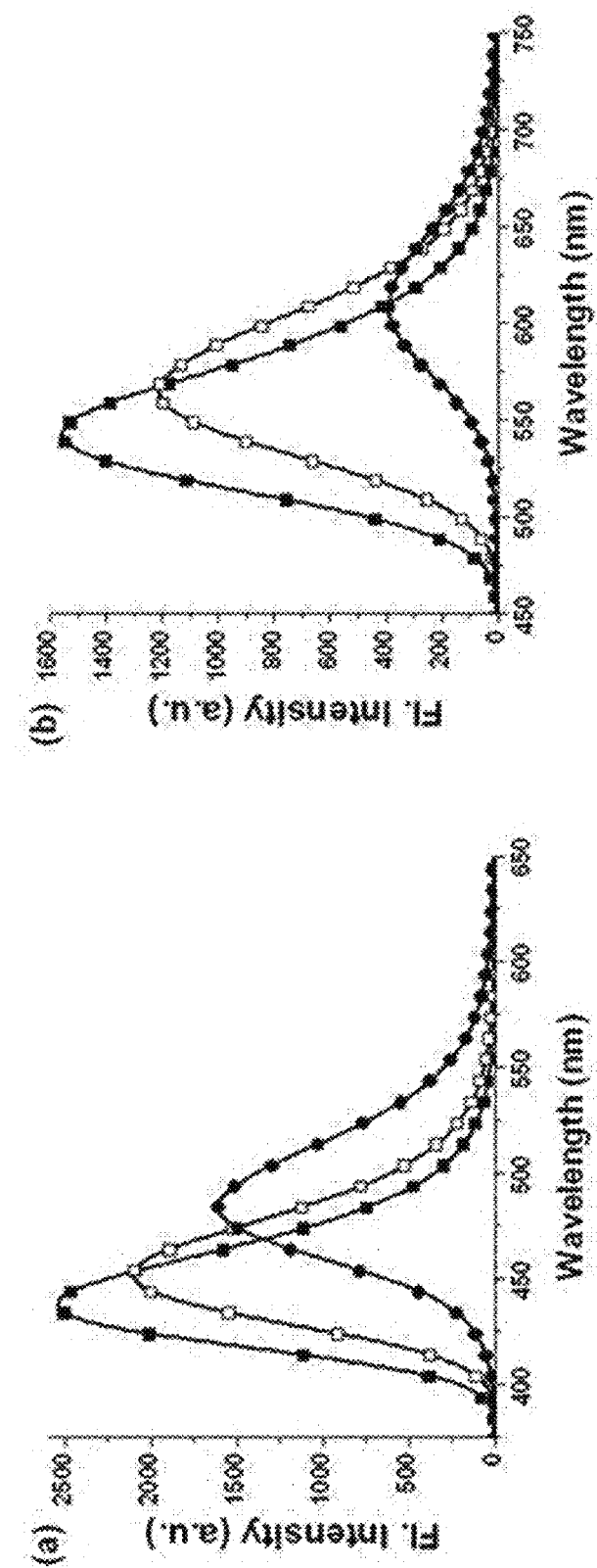
FIG. 13 illustrates fluorescence emission spectra of acedan (A) and compound 4a ($R_1=R_2=Me$) (B) having a concentration of 10 μM in a dichloromethane (■), acetonitrile (□), and ethanol (○) solution.

Quartz cells having a path length of 1 cm were filled with a dichloromethane, acetonitrile, ethanol (1%-DMSO included) and PBS buffer solution (10 mM, pH 7.4, 0.1%-DMSO included) which included compound 4a ($R_1$=$R_2$=Me) having a concentration of 1 μM to measure fluorescence spectra. The results thereof with fluorescence intensity as a y-axis and light wavelength as an x-axis are shown in FIGS. 2(B) and 13. Referring to FIGS. 2(B) and 13, it may be determined that the maximum emission wavelength ($\lambda_{em}$ (nm)) of the compound 4a ($R_1$=$R_2$=Me) which is a two-photon absorbing fluorophore according to the embodiment of the present invention was longer than that of conventional acedan (compound 1) known as a conventional two-photon absorbing fluorophore.

Figure 4:
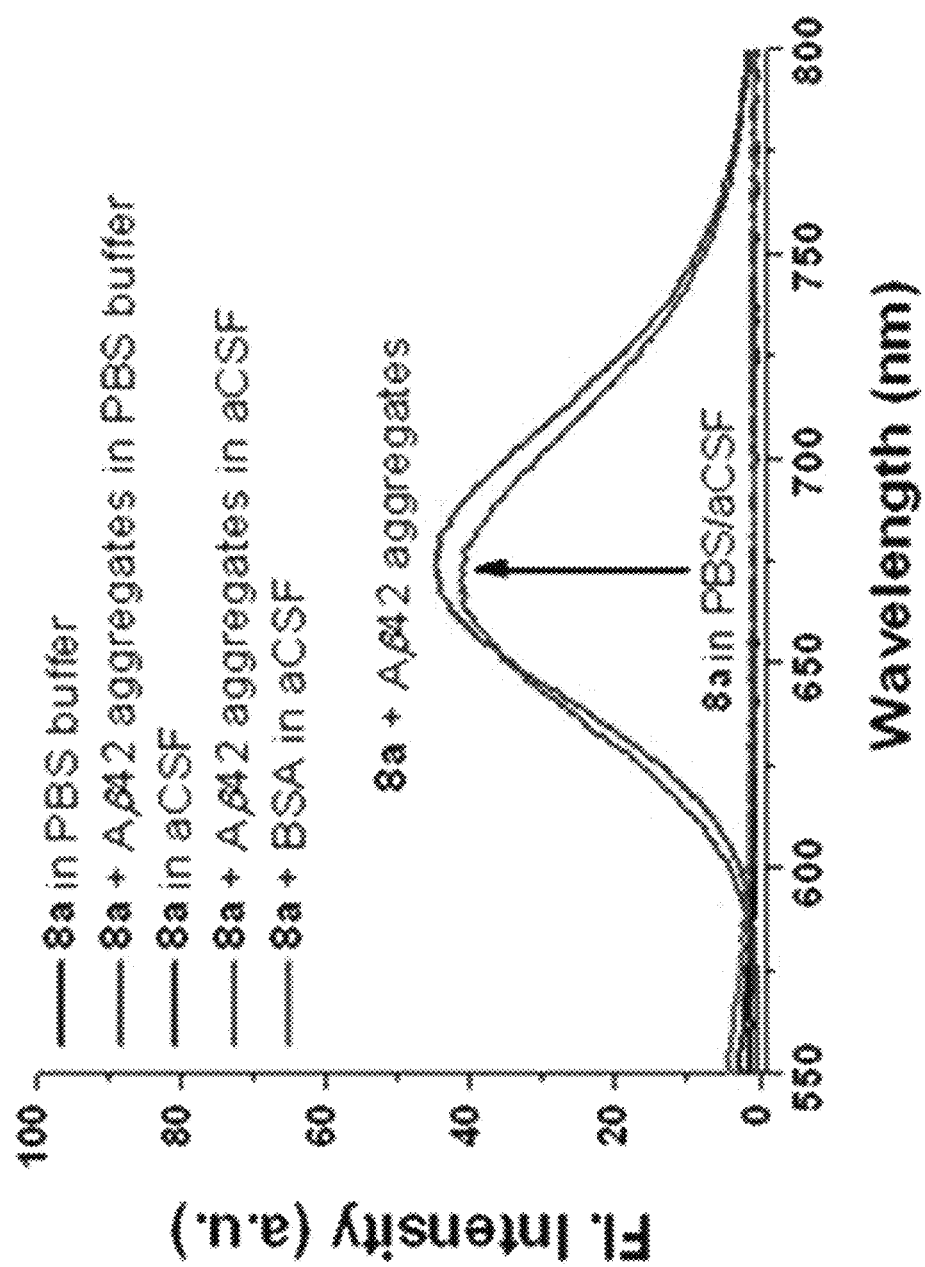
FIG. 4 illustrates fluorescence emission spectra of compound 8a ($R_1=R_2=Me$) having a concentration of 10 μM according to the presence of amyloid beta 42 (Aβ42, 20 μM) and bovine serum albumin (BSA, 20 μg/mL) in a PBS buffer solution (10 mM, pH 7.4, 0.1%-DMSO included) or an artificial cerebrospinal fluid (aCSF, 1%-DMSO included)

Quartz cells having a path length of 1 cm were filled with a PBS buffer solution (10 mM, pH 7.4, 0.1%-DMSO included) or an artificial cerebrospinal fluid (NaCl (124 mM), KCl (3 mM), $NaH_2PO_4$ (1.25 mM), $MgCl_2$ (1 mM), $NaHCO_3$ (36 mM), D-gluocose (10 mM), $CaCl_2$ (2 mM), 95%-$O_2$, 5%-$CO_2$ (by bubbler), aCSF and 1%-DMSO included) which included the compound 8a ($R_1$=$R_2$=Me) having a concentration of 10 μM to measure fluorescence spectra according to the presence of amyloid beta 42 (Aβ 42) and bovine serum albumin (BSA, 20 μg/mL), and the result is shown in FIG. 4. Referring to FIG. 4, it may be determined that the fluorescence intensity of the compound 8a ($R_1$=$R_2$=Me) was low when an amyloid beta plaque was absent, and the fluorescence intensity of the compound 8a ($R_1$=$R_2$=Me) increased when an amyloid beta plaque was present. Accordingly, it may be determined that the compound 8a ($R_1$=$R_2$=Me) selectively detected an amyloid beta plaque.

Further, the fluorescence quantum yield was measured with respect to an ethanol solution including the compounds 4a to 8a ($R_1$=$R_2$=Me) having a concentration of 10 μM, and the result is shown in FIG. 6. Acedan which is mainly used was used as a comparative compound (fluorescence quantum yield, $\Phi_F$=0.52, measured in ethanol solution).

Figure 8:
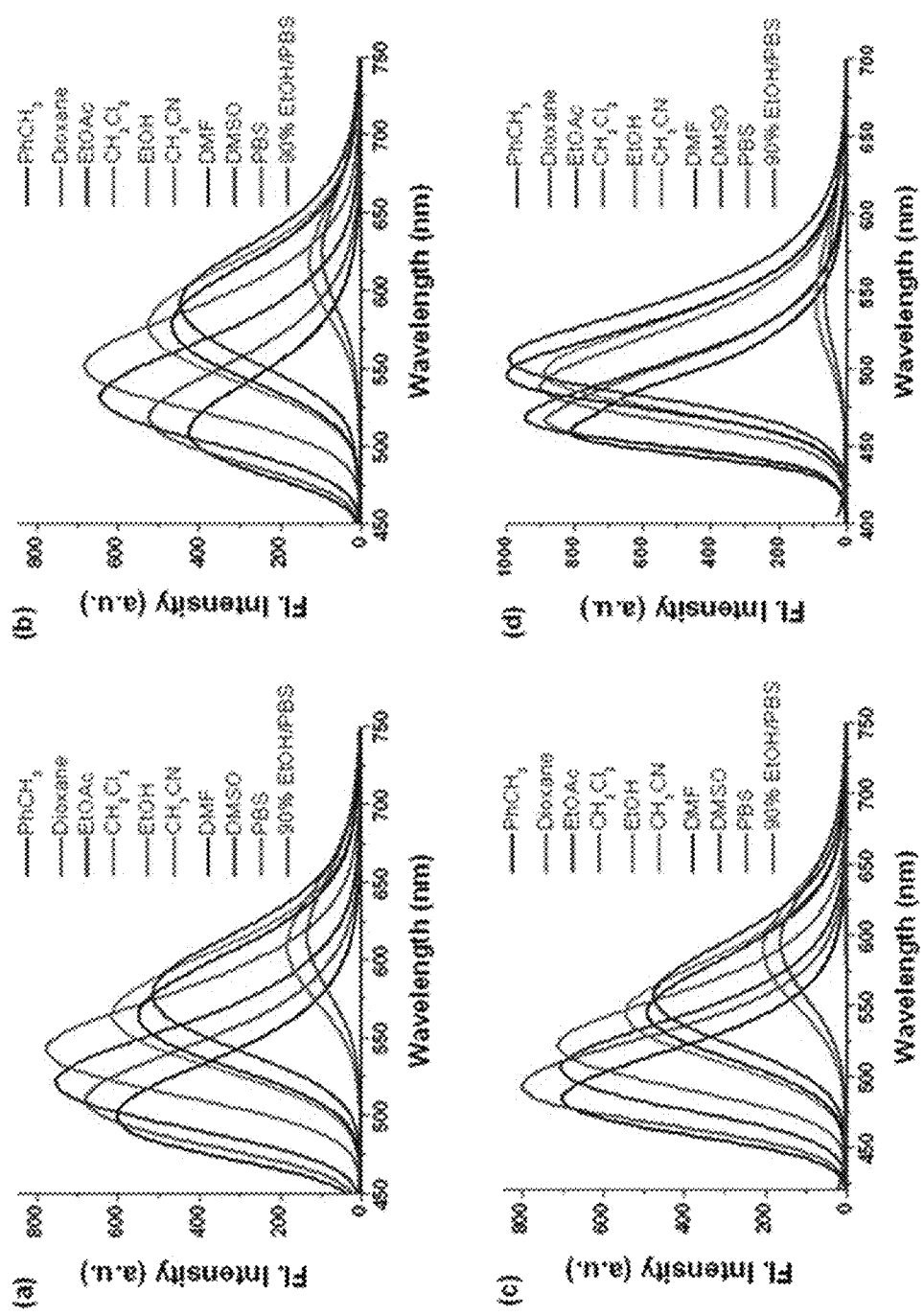
FIG. 8 illustrates fluorescence emission spectra (A, B, C and D, respectively) of compound 4a ($R_1=R_2=Me$), compound 5a ($R_1=R_2=Me$), compound 6a ($R_1=R_2=Me$), and compound 7a ($R_1=R_2=Me$) in toluene, dioxane, ethyl acetate, dichloromethane, ethanol, dimethylformamide, DMSO, a PBS buffer solution, and a 90%-ethanol/PBS buffer solution.
Figure 9:
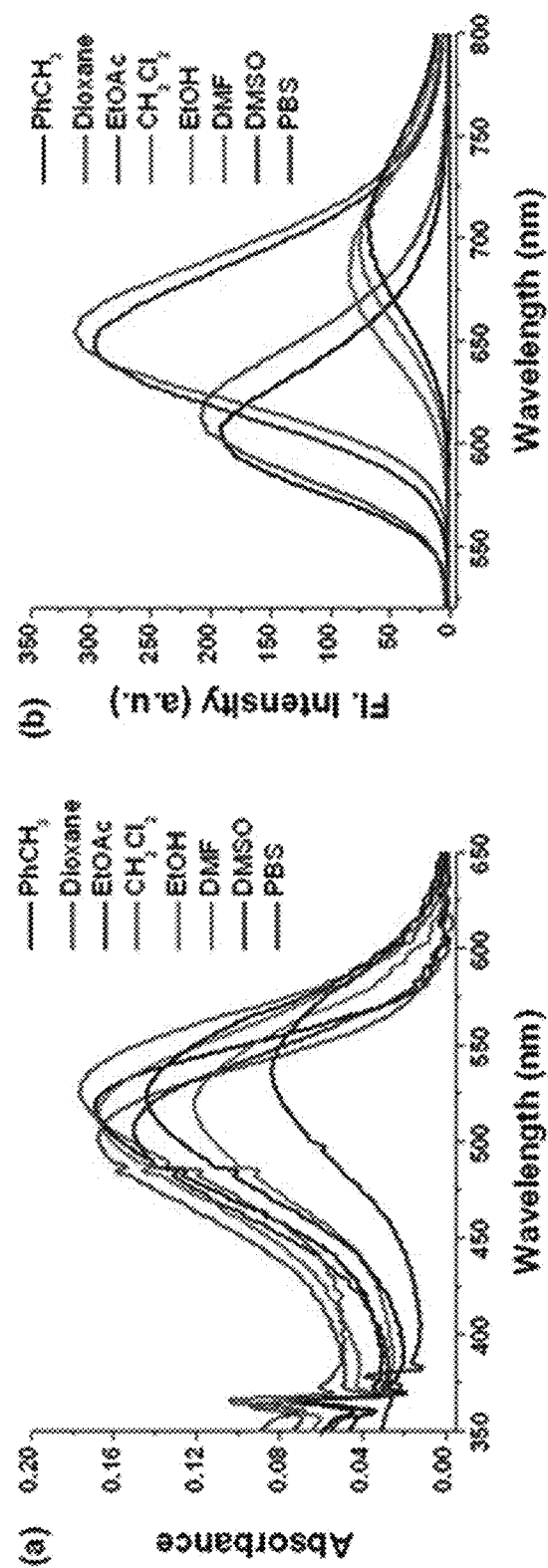
FIG. 9 illustrates absorption spectra (A) and fluorescence emission spectra (B) of compound 8a ($R_1=R_2=Me$) having a concentration of 10 μM in toluene, dioxane, ethyl acetate, dichloromethane, ethanol, acetonitrile, dimethylformamide, DMSO, and a PBS buffer solution.
Figure 10:
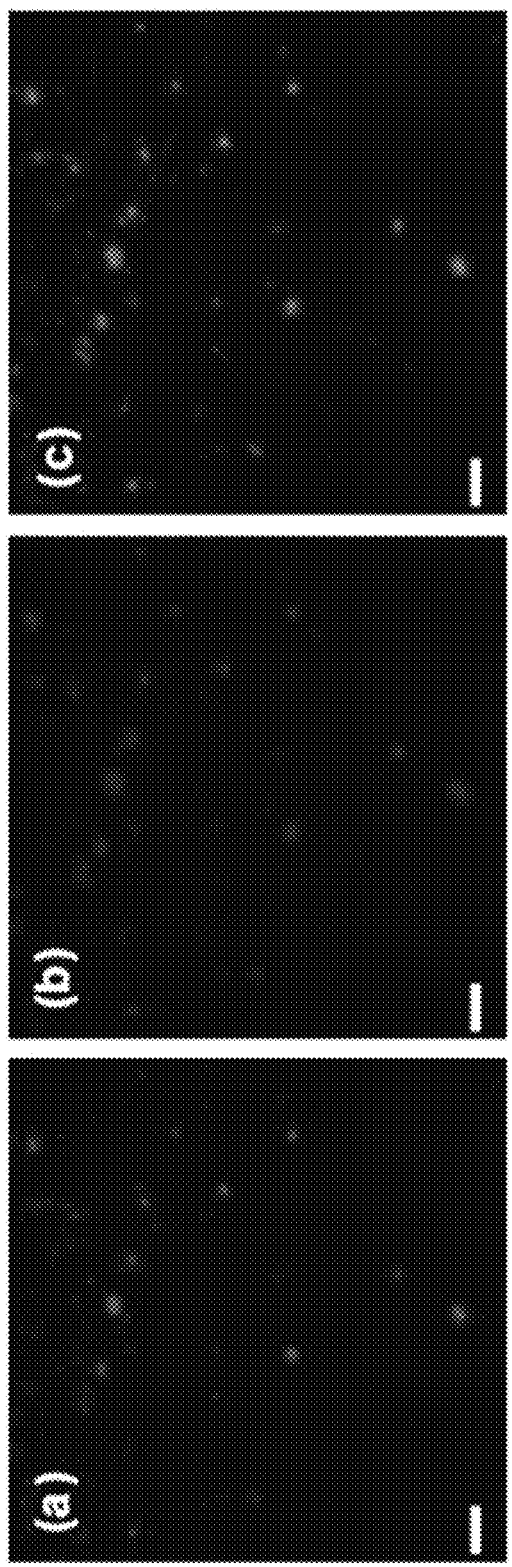
FIG. 10 illustrates a two-photon fluorescence microscope image (A) of the frontal cortex of 13-month-old mice (5XFAD mice) with Alzheimer's disease, which is taken when excited with light at a wavelength of 1,000 nm after the mice were intraperitoneally injected with compound 8a ($R_1=R_2=Me$) of 30 mg/kg, a two-photon fluorescence microscope image (B) of the frontal cortex of 13-month-old mice (5XFAD mice) with Alzheimer's disease, which is taken when excited with light at a wavelength of 780 nm after the mice were intraperitoneally injected with a compound MeO-X04 of 10 mg/kg, and an image (C) which is a combination of the images (A) and (B)

In order to determine the fluorescent properties of the compounds 4a to 7a ($R_1$=$R_2$=Me), quartz cells having a path length of 1 cm were filled with toluene, dioxane, ethyl acetate, dichloromethane, ethanol, acetonitrile, dimethylformamide, DMSO, a PBS buffer solution and a 90%-ethanol/PBS buffer solution (1%-DMSO included) which included the compounds 4a to 7a ($R_1$=$R_2$=Me) having a concentration of 10 μM to measure fluorescence spectra. The results thereof with fluorescence intensity as a y-axis and light wavelength as an x-axis are shown in FIG. 8. Further, in order to determine the fluorescent properties of the compound 8a ($R_1$=$R_2$=Me), quartz cells having a path length of 1 cm were filled with toluene, dioxane, ethyl acetate, dichloromethane, ethanol, dimethylformamide, DMSO and a PBS buffer solution to measure fluorescence spectra which included the compound 8a ($R_1$=$R_2$=Me) having a concentration of 10 μM. The results thereof with fluorescence intensity as a y-axis and light wavelength as an x-axis are shown in FIG. 9.

Figure 14:
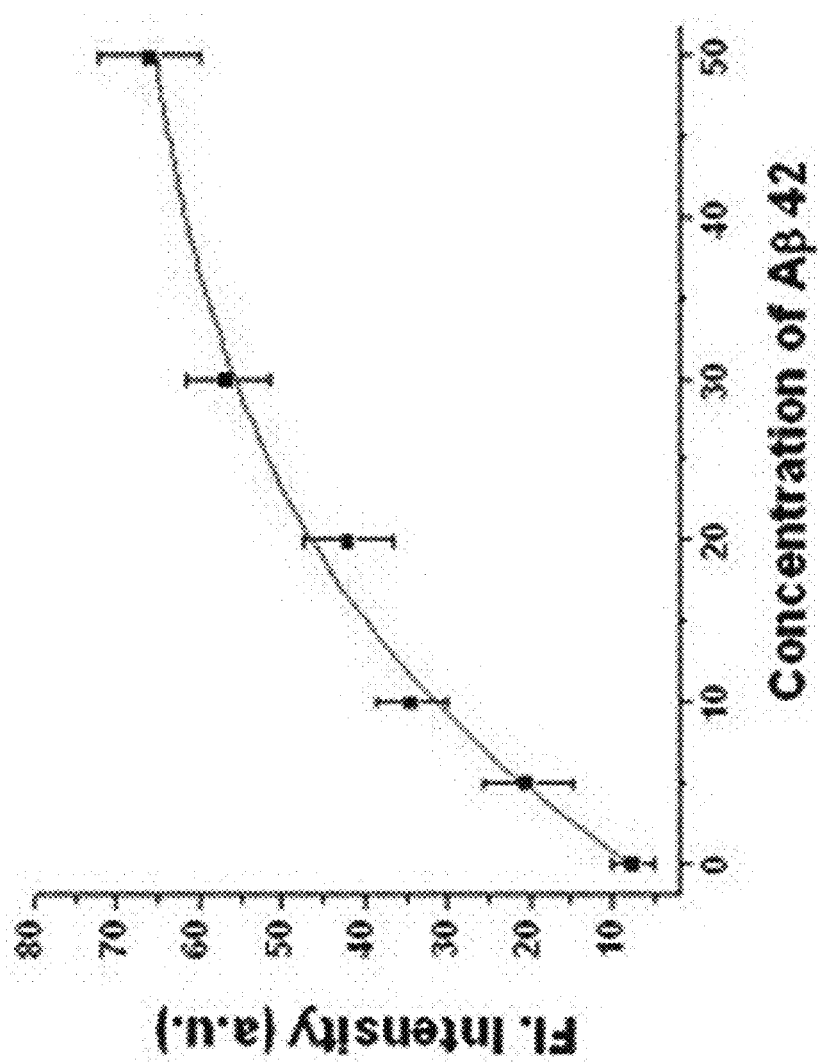
FIG. 14 illustrates the fluorescence intensity of compound 8a ($R_1=R_2=Me$) having a concentration of 10 μM at a maximum emission wavelength, which is measured when excited with light at a wavelength of 500 nm according to a concentration of amyloid beta 42 (Aβ 42)

In order to determine the fluorescent properties (y-axis) of the compound 8a ($R_1$=$R_2$=Me) according to the concentration of an amyloid beta plaque (x-axis), quartz cells having a path length of 1 cm were filled with a PBS buffer solution (1%-DMSO included) which included the compound 8a ($R_1$=$R_2$=Me) having a concentration of 10 μM and an amyloid beta plaque (0-50 μM) to measure fluorescence spectra, and the result is shown in FIG. 14.

Figure 15:
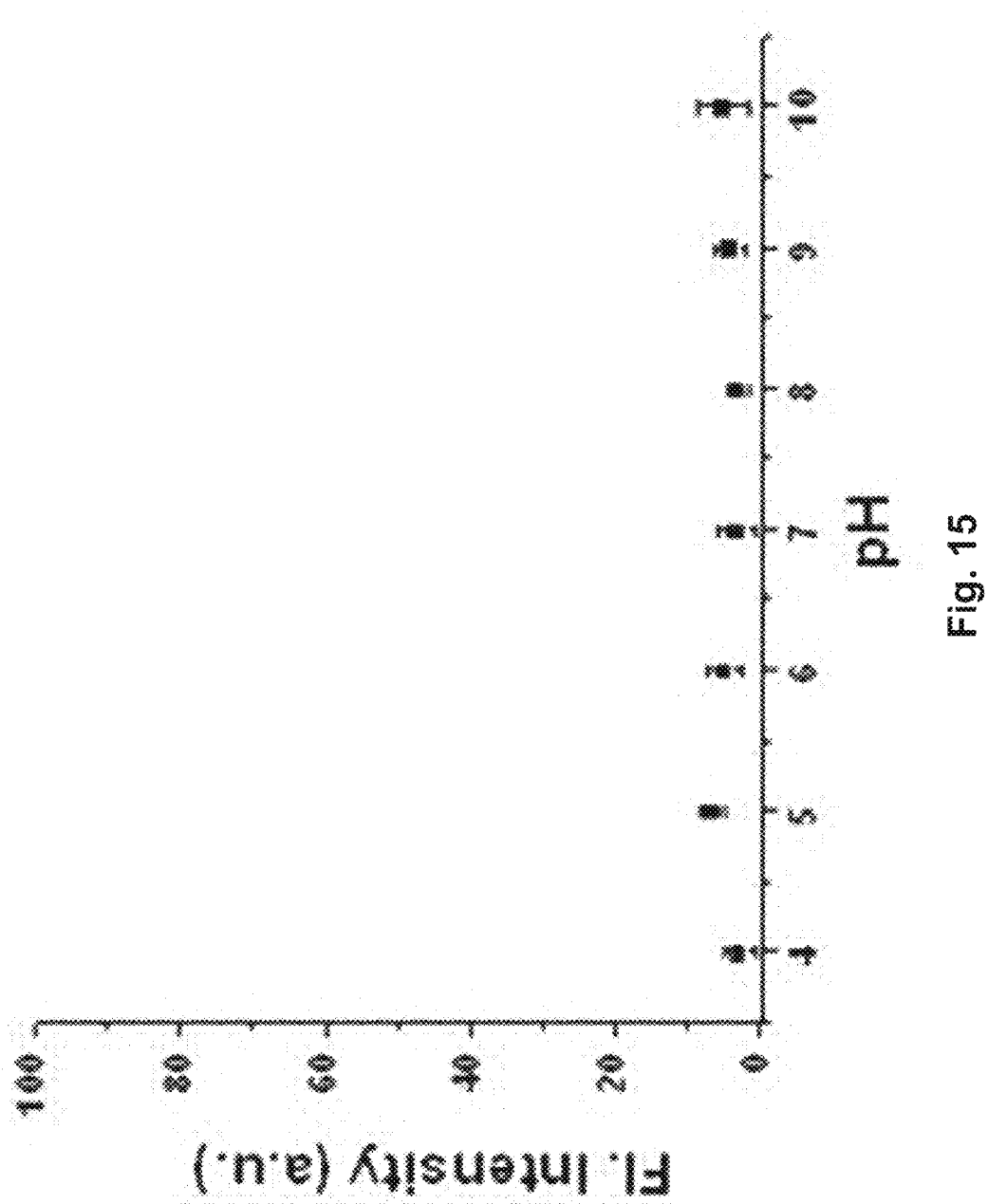
FIG. 15 illustrates the fluorescence intensity of compound 8a ($R_1=R_2=Me$) having a concentration of 10 μM at a maximum emission wavelength, which is measured when excited with light at a wavelength of 500 nm according to a pH in the range of 4 to 10.

In order to determine the fluorescent properties (y-axis) of the compound 8a ($R_1$=$R_2$=Me) according to the pH (x-axis), quartz cells having a path length of 1 cm were filled with an aqueous solution (1%-DMSO included) which has a pH in the range of 4 to 10 and included the compound 8a ($R_1$=$R_2$=Me) having a concentration of 10 μM to measure the fluorescence spectrum, and the result is shown in FIG. 15. Referring to FIG. 15, it may be determined that the fluorescence intensity of the compound 8a ($R_1$=$R_2$=Me) was low regardless of pH, and the change in the fluorescence intensity of the compound 8a ($R_1$=$R_2$=Me) according to pH was not shown.

Example 8

Two-Photon Absorption Properties of Compound 4a ($R_1$=$R_2$=Me) and Compound 8a ($R_1$=$R_2$=Me)

Figure 16:
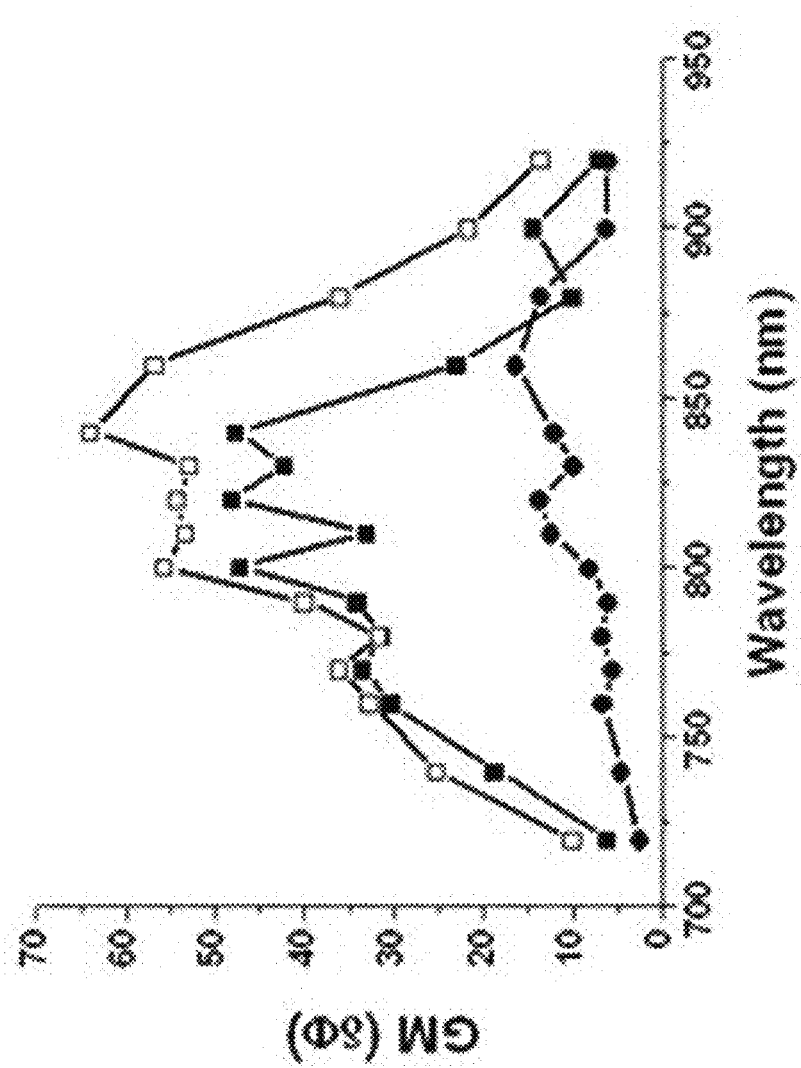
FIG. 16 illustrates two-photon action spectra of compound 4a ($R_1=R_2=Me$) having a concentration of 10 μM in toluene (■), dimethylformamide (□), and ethanol (●) at a laser power of 150 mW (at a focal point)
Figure 17:
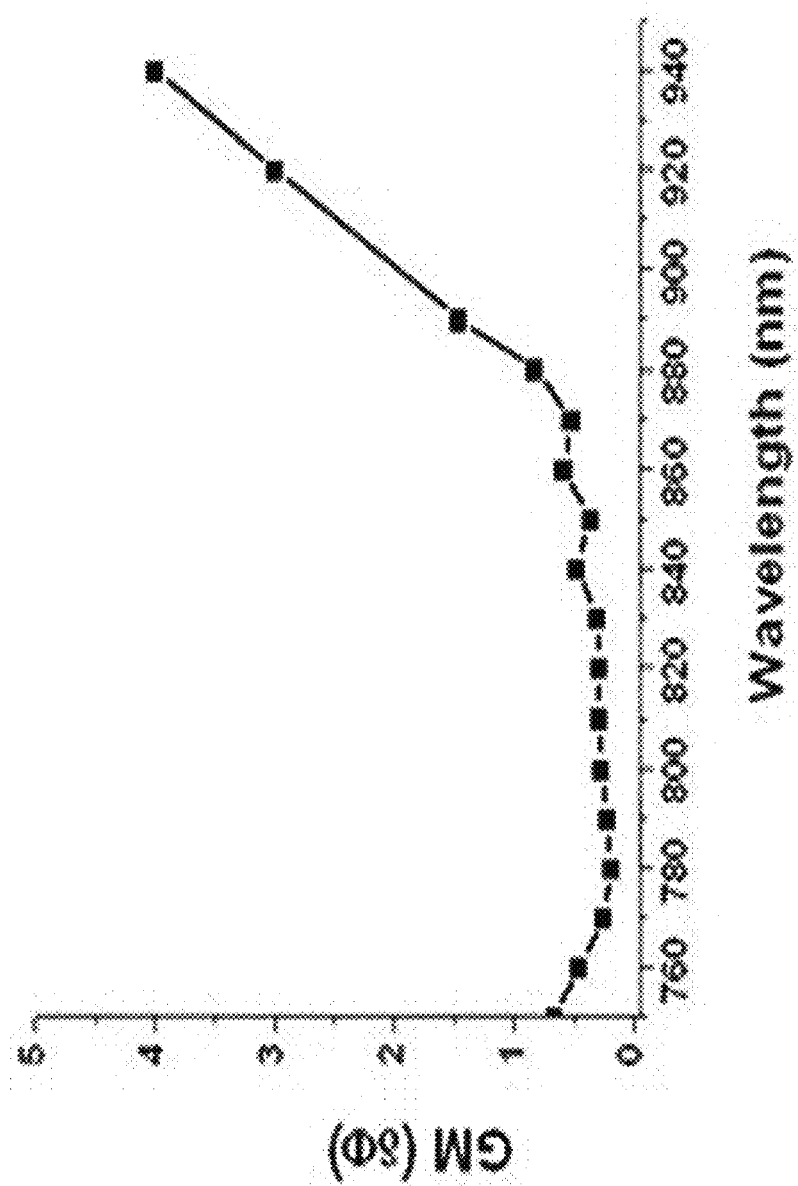
FIG. 17 illustrates two-photon action spectra of compound 8a ($R_1=R_2=Me$) having a concentration of 10 μM in ethanol at a laser power of 150 mW (at a focal point)

The inventors of the present invention determined the two-photon absorption properties by two-photon excitation of the compound 4a ($R_1$=$R_2$=Me) and the compound 8a ($R_1$=$R_2$=Me) which are two-photon absorbing fluorophores according to the embodiment of the present invention, and the results are shown in FIGS. 16 and 17.

More specifically, in order to determine the two-photon absorption properties of the compound 4a ($R_1$=$R_2$=Me) which is a two-photon absorbing fluorophore, the inventors of the present invention measured a two-photon action cross section ($\Phi_\delta$) with respect to a toluene (■), dimethylformamide (□) and ethanol solution (1%-DMSO included) (●) which included the compound 4a ($R_1$=$R_2$=Me) having a concentration of 10 μM, and two-photon action spectra are shown in FIG. 16. Further, in order to determine the two-photon absorption properties of the compound 8a ($R_1$=$R_2$=Me), the two-photon absorption efficiency was measured with respect to an ethanol solution which included the compound 8a ($R_1$=$R_2$=Me) having a concentration of 10 μM, and the spectrum is shown in FIG. 17. The two-photon absorption efficiency was measured using a two-photon induced fluorescence method, and 1 GM refers to $10^{-50}$ cm$^4$ s photon$^{-1}$ molecule$^{-1}$. In FIGS. 16 and 17, it may be determined that the two-photon absorption efficiency value of the compound 4a ($R_1=R_2=$Me) in a long wavelength (>850 nm) and the two-photon absorption efficiency value of the compound 8a ($R_1=R_2=$Me) in a long wavelength (>900 nm) were lower than that (~100 GM) of conventional acedan. However, referring to FIGS. 3, 5, and 17, it may be found that the two-photon absorption efficiency value of the compound 4a ($R_1=R_2=$Me) in a long wavelength (>850 nm) and the two-photon absorption efficiency value of the compound 8a ($R_1=R_2=$Me) in a long wavelength (>900 nm) were more suitable to obtain a clear two-photon microscope image. This shows that the effect from autofluorescence of a fluorophore in vivo can be suppressed sufficiently.

Example 9

Observation of Two-Photon Microscope Image of Tissue of Mice Treated with Compound 4a ($R_1=R_2=$Me) and Compound 8a ($R_1=R_2=$Me)

The inventors of the present invention treated the tissue of mice with the compound 4a ($R_1=R_2=$Me) and the compound 8a ($R_1=R_2=$Me) according to the embodiment of the present invention and observed the fluorescence intensity using a two-photon microscope, and the results are shown in FIGS. 3, 5, 10 and 18.

Figure 3:
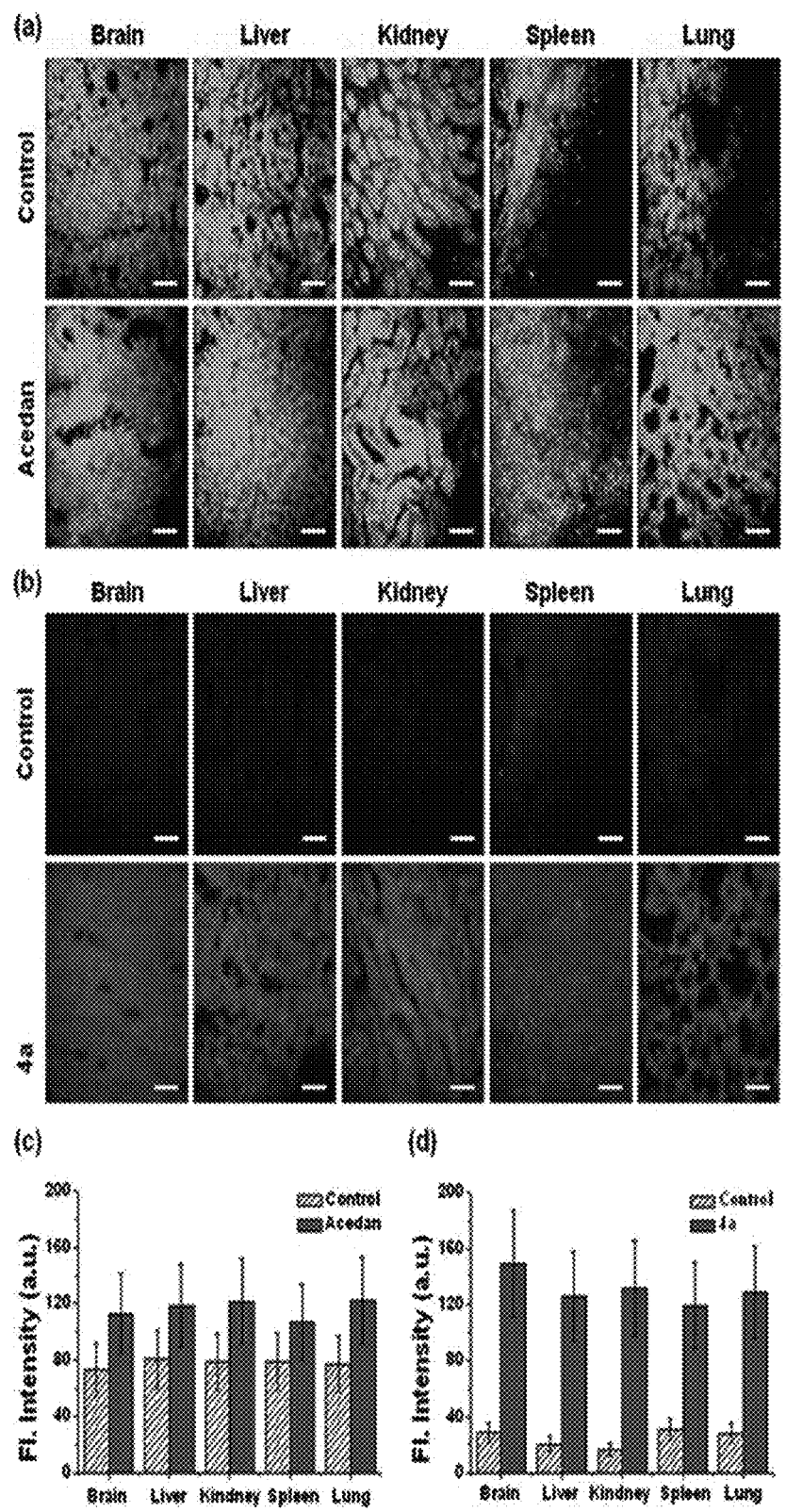
FIG. 3 illustrates two-photon fluorescence microscope Images (A) taken when the brain, liver, kidney, spleen, and lung tissue of mice treated with acedan having a concentration of 10 μM are excited with light at a wavelength of 780 nm, two-photon fluorescence microscope images (B) taken when the brain, liver, kidney, spleen, and lung tissue of mice treated with compound 4a ($R_1=R_2=Me$) having a concentration of 10 μM are excited with light at a wavelength of 900 nm, and relative intensities of fluorescence in the electron microscope images of the acedan having a concentration of 10 μM and the compound 4a ($R_1=R_2=Me$) having a concentration of 10 μM ((C) And (D), respectively)

More specifically, in order to observe the two-photon microscope image of tissue of mice treated with the compound 4a ($R_1=R_2=$Me), C57BL6 mice (5-weeks-old, male, Samtako Inc.) were used, and the experiment was performed under the condition of darkness (darkroom). The brain, liver, kidney, spleen and lung tissue of mice were dissected, were cleaned using a PBS buffer solution, and each organ was frozen using dry-ice for 5 minutes. The frozen organs were broken using a hammer, and a tissue slice sample having a thickness of 16 μm was prepared using a cryostat machine (Leica, CM3000 model). An optical cutting temperature compound (OCT, 10%-polyvinyl alcohol, 25%-polyethylene glycol and 85.5%-inactive species) was used to fix the organs to the cryostat machine. The sliced tissue sample was laid on a specimen block (Paul Marienfeld GMbH & Co.), the specimen block was immersed in 4%-paraformaldehyde for 10 minutes and was cleaned using a PBS buffer solution, and then the tissue was fixed again using a mounting solution (Gel Mount, Biomeda Corporation). The prepared sliced tissue sample was immersed in a PBS buffer solution which included the compound 4a ($R_1=R_2=$Me) having a concentration of 10 μM and acedan for 10 minutes, was cleaned three times using a PBS buffer solution, and then was fixed in 4%-paraformaldehyde to observe fluorescence. The two-photon microscope including an upright microscope (BX51, Olympus Corporation), 20-fold and 40-fold objective lenses (XLUMPLEN, NA 1.0, Olympus Corporation), and a Ti: Sapphire laser (Chameleon Ultra II, Coherent Inc.) was used. The fluorescence was observed at a laser power of 10 mW and two-photon excitation wavelengths of 780 nm (acedan) and 900 nm (compound 4a ($R_1=R_2=$Me)). Referring to FIG. 3, it may be determined that the two-photon microscope image of the compound 4a ($R_1=R_2=$Me) according to the embodiment of the present invention provides a more clear image with a higher contrast as compared to that of conventional acedan in a suitable biological optical window area (800 to 1,000 nm). Further, contrary to the image obtained using acedan (FIG. 3(A)), it may be determined that the effect from autofluorescence was sufficiently suppressed in the image obtained using the compound 4a ($R_1=R_2=$Me) (FIG. 3(B)).

In order to observe the two-photon microscope image of tissue of mice treated with the compound 8a ($R_1=R_2=$Me), 5XFAD mice (13-months-old, The Jackson Laboratory, Bar Harbor, Me., USA; stock no. 006554, Tg6799) were used. An amyloid beta plaque is shown as a typical characteristic of Alzheimer's disease.

All animal experiments were performed after the approval from an animal testing ethics committee. In an open-skull craniotomy surgery, imaging was performed after treatment with the compound 8a ($R_1=R_2=$Me) and MeO-X04 which is a well-known amyloid beta plaque fluorophore. The mice were fixed on a stereotactic heating surface using Zoletil 50 (Virbac; intramuscular injection, 0.03 mL) as an anesthetic agent (Seoul, Republic of Korea, 37° C.). After a scalp and periosteum were removed, a hole having a diameter of 3 mm was formed at a distance 1 mm from the bregma and 1 mm from the sagittal suture of a skull, a bone was removed, and then a round coverslip was adhered thereto using Loctite 454. The exposed portion of the skull was covered with a dental acrylic, and dexamethasone (0.2 mg/kg) and carprofen (5 mg/kg) which are anti-inflammatory drugs were used before and after the surgery.

Figure 5:
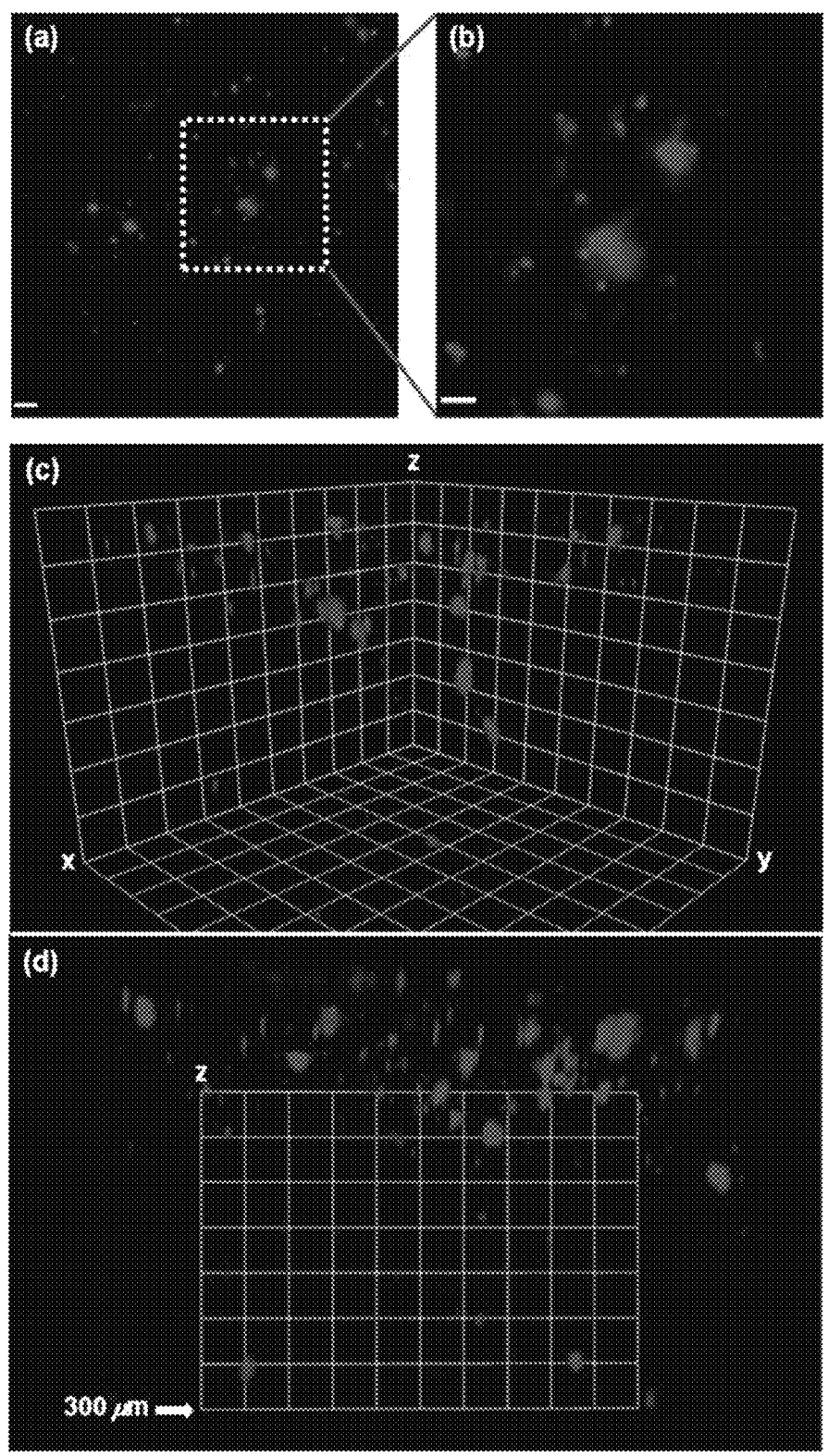
FIG. 5 illustrates a two-photon fluorescence microscope image (A), a 60× enlarged image (B) and two-photon fluorescence microscope images reconstructed in 3-dimension (3-D) (C and D) of frontal cortex of 13-month-old mice (5XFAD mice) with Alzheimer's disease, which are taken when excited with light at a wavelength of 1,000 nm after the mice were intraperitoneally injected with compound 8a ($R_1=R_2=Me$) of 30 mg/kg.
Figure 18:
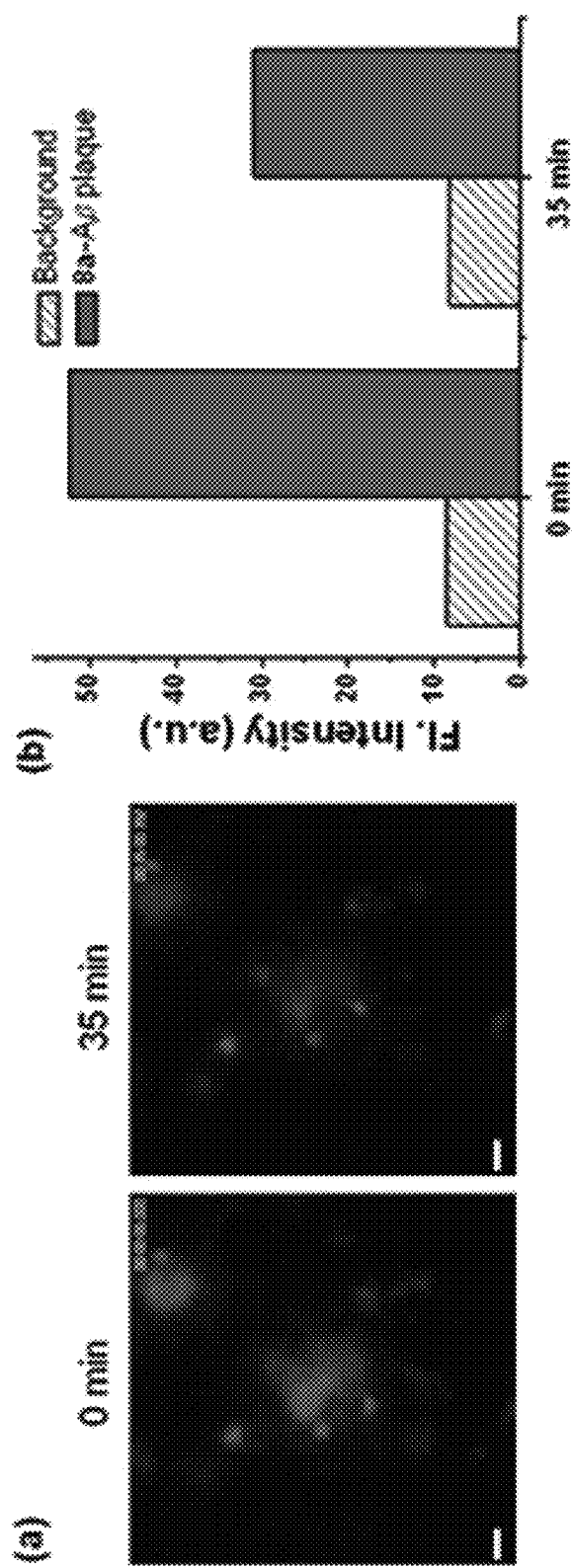
FIG. 18 illustrates images of a photo-bleaching process (A) and relative fluorescence intensities in electron microscope images (B) before and after irradiation with a two-photon light source with respect to compound 8a ($R_1=R_2=Me$) and a complex compound of amyloid beta plaque in a tissue at a depth of 50 μm in an animal model with Alzheimer's disease.

A product manufactured by Carl Zeiss Microscopy GmbH (Oberkochen, Germany; model no. LSM 7 MP two-photon laser scanning microscope system) was used as a two-photon microscope. In order to visualize an amyloid beta plaque and test the compound 8a ($R_1=R_2=$Me), the intraperitoneal injection of the compound 8a ($R_1=R_2=$Me) (30 mg/kg; 10%-storage solution (50 mg/mL DMSO), 45%-propylene glycol, 45%-PBS) and MeO-X04 (10 mg/kg; 10%-storage solution (50 mg/mL DMSO), 45%-propylene glycol, 45%-PBS) were performed 24 hours before imaging. A two-photon microscope image was observed at a laser power of 50 mW and two-photon excitation wavelengths of 780 nm (MeO-X04) (FIG. 10(B)) and 1,000 nm (compound 8a ($R_1=R_2=$Me)) (FIG. 10(A)). Referring to a combined image (FIG. 10(C)), it may be determined that the conformity between the image result (FIG. 10(B)) in which the treatment with MeO-X04 which is well-known as an amyloid beta plaque fluorophore was performed and the image result (FIG. 10(A)) in which the treatment with the compound 8a ($R_1=R_2=$Me) was performed was significantly high, and thus the compound 8a ($R_1=R_2=$Me) may selectively visualize an amyloid beta plaque. In order to obtain a three-dimensional image, an image collection to a depth of 300 μm was performed at an interval of 1 μm with respect to a z-axis, the image processing was performed using Volocity software (PerkinElmer Inc., MA, USA), and the result is shown in FIG. 5. Referring to FIG. 5, it may be determined that the compound 8a ($R_1=R_2=$Me) may selectively visualize an amyloid beta plaque in an animal model with Alzheimer's disease (FIGS. 5(A) and 5(B)) and may visualize an amyloid beta plaque as a three-dimensional image (FIGS. 5(C) and 5(D)). Further, the photo-bleaching process images and the relative fluorescence intensity in electron microscope images before and after irradiation with a light source with respect to the compound 8a ($R_1=R_2=$Me) and a complex compound of an amyloid beta plaque are shown in FIG. 18. Referring to FIG. 18, it may be determined that the fluorescence intensity of the compound 8a ($R_1=R_2=$Me) decreased about 40% when irradiated with a two-photon light source for 35 minutes. Accordingly, it could be found that the compound 8a ($R_1=R_2=$Me) may visualize an amyloid beta plaque in an animal model with Alzheimer's disease for a long time.

Example 10

Determination of Cytotoxicity of Cells Treated with Compound 4a ($R_1=R_2=Me$) and Compound 8a ($R_1=R_2=Me$)

Figure 19:
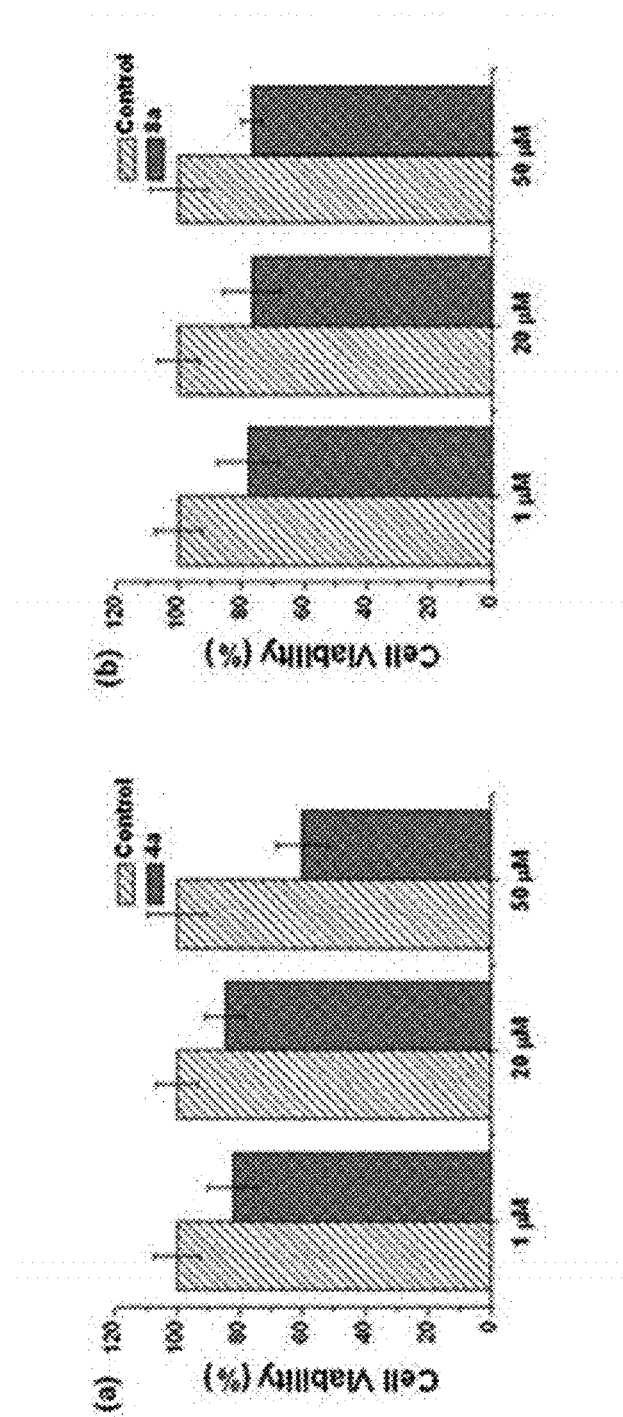
FIG. 19 illustrates the cell viability of SHSY5Y cells treated with compound 4a ($R_1=R_2=Me$)(a) and compound 8a ($R_1=R_2=Me$)(b) each having a concentration of 1, 20 and 50 μM.

The inventors of the present invention treated SHSY5Y cells with the compound 4a ($R_1=R_2=Me$) and the compound 8a ($R_1=R_2=Me$) to determine cytotoxicity, and the results are shown in FIG. 19.

In order to determine the cytotoxicity of cells treated with the compound 4a ($R_1=R_2=Me$) and the compound 8a ($R_1=R_2=Me$), the metabolic capability of a formazan of SHSY5Y cells with respect to 3-(4,5-dimethyldiazol-2-yl)-2,5-diphenyltetrazolium bromide (MTT) was evaluated.

More specifically, the cells (100 μL/well) were prepared with the density of about $5\times10^3$ cells in each well on a 96-well plate. The cells were treated with the compound 4a ($R_1=R_2=Me$) and the compound 8a ($R_1=R_2=Me$) each having concentrations of 1, 20 and 50 μM, was incubated for 1 hour, were cleaned using a PBS buffer solution, and 25 μL of a MTT solution (5 mg/mL) was added to each well. After the cells were incubated at 37° C. for 2 hours, the media was removed, and a formazan crystal was dissolved in DMSO to measure absorbance using a plate reader. Referring to FIG. 19(A), it may be determined that the compound 4a ($R_1=R_2=Me$) having concentrations of 1 μM and 20 μM shows low cytotoxicity (20% apoptosis). Referring to FIG. 19(B), it may be determined that the compound 8a (R1=R2=Me) having concentrations of 1 to 50 μM shows low cytotoxicity (20% apoptosis). Accordingly, it may be determined that the cytotoxicity of the compound 4a ($R_1=R_2=Me$) and the compound 8a ($R_1=R_2=Me$) was low to be suitable for obtaining a two-photon microscope image in tissue and an animal model.

Since the two-photon absorbing fluorophore according to the embodiment of the present invention has a longer absorption wavelength and emission wavelength than acedan and its derivatives which are conventional two-photon absorbing fluorophores, the effect from autofluorescence can be minimized, and a clear image with high resolution can be obtained. Accordingly, the two-photon absorbing fluorophore according to the embodiment of the present invention is expected to be useful for imaging studies.

Further, the two-photon absorbing fluorophore according to the embodiment of the present invention is expected to be suitable for realizing an image with high resolution in a deep tissue, and to be used as a fluorescent probe sensitive to a surrounding environment in a variety of applications in in-vivo imaging studies, such as imaging of amyloid-beta plaque in a living animal model with Alzheimer's disease, etc.

The above description for the present invention is merely for an example, and it will be apparent to those skilled in the art that various modifications can be made to the above-described exemplary embodiments of the present invention without departing from the spirit or scope of the invention. Thus, it is intended that the above-described embodiments of the present invention are merely exemplified in all aspects and the present invention is not limited thereto.

What is claimed is:

1. An acedan derivative represented by the following Formula 1:

[Formula 1]

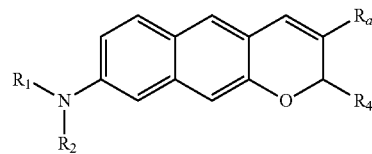

wherein, in Formula 1, $R_1$ and $R_2$ each are a hydrogen (H), a methyl (Me) group, an allyl group, an unsubstituted alkyl group having 2 to 12 carbon atoms, or a cyclic secondary amine;

$R_3$ is —(C=O)—$R_5$, —(C=O)H, —CH=C(CN)$_2$, or a cycloalkyl group formed with $R_4$;

$R_4$ is a hydrogen, or a cycloalkyl group formed with $R_3$, where the cycloalkyl group formed with $R_3$ and $R_4$ is

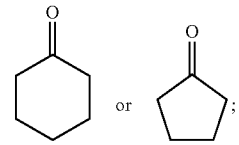 [SMILES: O=C1CCCCC1 ; O=C1CCCC1]

and $R_5$ is a methyl (Me), an ethyl, or an unsubstituted alkyl group having 2 to 12 carbon atoms.

2. The acedan derivative according to claim 1, wherein the acedan derivative is a compound selected from the group consisting of the compounds with the following Formulas 4 to 8:

[Formula 4]

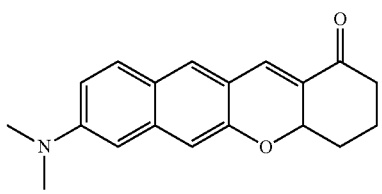

[Formula 5]

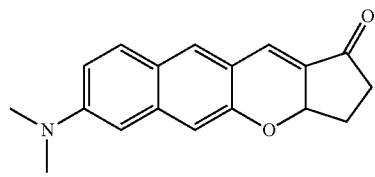

[Formula 6]

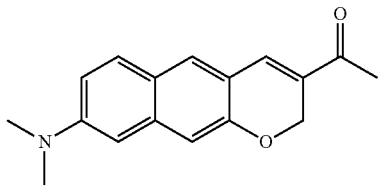

[Formula 7]

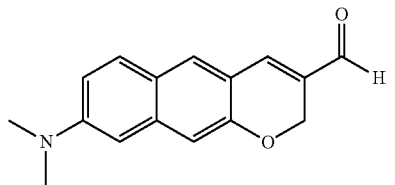

[Formula 8]

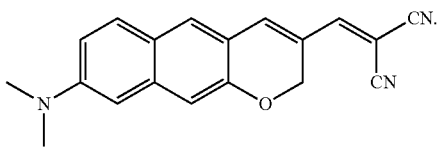

3. The acedan derivative according to claim 1, wherein the acedan derivative is a two-photon absorbing fluorophore.

4. A method for imaging a cell or tissue comprising:
treating a cell or tissue with the acedan derivative according to claim 1, and
observing the cell or tissue using a fluorescent microscope.

5. The method according to claim 4, wherein the imaging method is a method for imaging amyloid-beta plaque in a tissue.

6. The method according to claim 4, wherein the fluorescent microscope is a one-photon fluorescence microscope or a two-photon fluorescence microscope.

7. A method for diagnosing Alzheimer's disease, comprising administering the acedan derivative according to claim 1 to a subject in need thereof.

8. A method of preparing an acedan derivative represented by the Formula 4, according to claim 2, from 6-(dimethylamino)-3-hydroxy-2-naphthaldehyde, comprising synthesizing 8-(dimethylamino)-2,3,4a-tetrahydro-1H-benzo[b]xanthene-1-one by adding 2-cyclohexene-1-one and 1,4-diazabicyclo[2.2.2]octane to 6-(dimethylamino)-3-hydroxy-2-naphthaldehyde.

9. A method of preparing an acedan derivative represented by the Formula 5, according to claim 2, from 6-(dimethylamino)-3-hydroxy-2-naphthaldehyde, comprising synthesizing 7-(dimethylamino)-3,3a-dihydrobenzo[g]cyclopenta[b]chromene-1(2H)-one by adding 2-cyclopentene-1-one and 1,4-diazabicyclo[2.2.2]octane to 6-(dimethylamino)-3-hydroxy-2-naphthaldehyde.

10. A method of preparing an acedan derivative represented by the Formula 6, according to claim 2, from 6-(dimethylamino)-3-hydroxy-2-naphthaldehyde, comprising synthesizing 1-(8-(dimethylamino)-2H-benzo[g]chromene-3-yl)ethanone by adding 3-butene-2-one, magnesium iodide, tetramethylethylenediamine, and 4-dimethylaminopyridine to 6-(dimethylamino)-3-hydroxy-2-naphthaldehyde.

11. A method of preparing an acedan derivative represented by the Formula 7, according to claim 2, from 6-(dimethylamino)-3-hydroxy-2-naphthaldehyde, comprising synthesizing 6-(dimethylamino)-3-(propynyl-2-oxy)-2-naphthaldehyde by adding propargyl bromide and potassium carbonate to 6-(dimethylamino)-3-hydroxy-2-naphthaldehyde, and adding malononitrile and copper iodide thereto.

12. A method of preparing an acedan derivative represented by the Formula 8, according to claim 2, from 6-(dimethylamino)-3-(propynyl-2-oxy)-2-naphthaldehyde, comprising synthesizing 2-(((8-dimethylamino)-2H-benzo[g]chromene-3-yl)methylene)malononitrile by adding malononitrile, copper iodide, and triethylamine to 6-(dimethylamino)-3-(propynyl-2-oxy)-2-naphthaldehyde.

\* \* \* \* \*